（12）United States Patent
Nowak et al.

(10) Patent No.: US 10,876,025 B2
(45) Date of Patent: *Dec. 29, 2020

(54) BUGPHOBIC AND ICEPHOBIC COMPOSITIONS WITH LIQUID ADDITIVES

(71) Applicant: HRL Laboratories, LLC, Malibu, CA (US)

(72) Inventors: Andrew P. Nowak, Los Angeles, CA (US); April R. Rodriguez, Los Angeles, CA (US); Jason A. Graetz, Calabasas, CA (US); Adam F. Gross, Santa Monica, CA (US)

(73) Assignee: HRL Laboratories, LLC, Malibu, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 15/727,669

(22) Filed: Oct. 9, 2017

(65) Prior Publication Data

US 2018/0030329 A1    Feb. 1, 2018

Related U.S. Application Data

(63) Continuation-in-part of application No. 14/829,640, filed on Aug. 19, 2015, now Pat. No. 10,125,227,
(Continued)

(51) Int. Cl.
*C09K 5/10*    (2006.01)
*C09K 5/20*    (2006.01)
(Continued)

(52) U.S. Cl.
CPC ............... *C09K 5/20* (2013.01); *A01N 31/02* (2013.01); *C07C 31/18* (2013.01); *C08G 18/246* (2013.01);
(Continued)

(58) Field of Classification Search
CPC .............. C08G 18/246; C08G 18/3206; C08G 18/4833; C08G 18/5015; C08G 18/758; C09K 5/08; C09K 5/10
See application file for complete search history.

(56) References Cited

U.S. PATENT DOCUMENTS 3,435,003 A    3/1969 Craven
3,810,874 A    5/1974 Mitsch et al.
(Continued)

FOREIGN PATENT DOCUMENTS

| EP | 1558661 B1 | 12/2012 |
|---|---|---|
| WO | 1997035919 A1 | 10/1997 |
| WO | 2013158360 A1 | 10/2013 |

OTHER PUBLICATIONS

"Reduced Phase Separation and Slowing of Dynamics in Polyurethanes with Three-Dimensional POSS-Based Crosslinking Moieties" Raftopoulos et al. Macromolecules, 2015, 48, 1429-1441.*
(Continued)

*Primary Examiner* — Michael L Leonard
(74) *Attorney, Agent, or Firm* — O'Connor & Company

(57) ABSTRACT

Some variations provide a composition comprising: a first solid material and a second solid material that are chemically distinct and microphase-separated; and at least one liquid selectively absorbed into either of the first solid material or the second solid material. The first and second solid materials are preferably present as phase-separated regions of a copolymer, such as in a segmented copolymer (e.g., a urethane-urea copolymer). The liquid may be a freezing-point depressant for water. For example, the liquid may be selected from methanol, ethanol, isopropanol, ethylene glycol, propylene glycol, or glycerol. The liquid may be a lubricant. For example, the liquid may be selected from fluorinated oils, siloxanes, petroleum-derived oils, mineral oil, or plant-derived oils. The liquid may consist of or
(Continued)

include water. The liquid may be an electrolyte. For example, the liquid may be selected from poly(ethylene glycol), ionic liquids, dimethyl carbonate, diethyl carbonate, or methyl ethyl dicarbonate.

**24 Claims, 11 Drawing Sheets
(6 of 11 Drawing Sheet(s) Filed in Color)**

Related U.S. Application Data which is a continuation-in-part of application No. 14/658,188, filed on Mar. 14, 2015.

(60) Provisional application No. 62/408,280, filed on Oct. 14, 2016, provisional application No. 62/038,878, filed on Aug. 19, 2014, provisional application No. 61/950,093, filed on Mar. 14, 2014.

(51) Int. Cl.
| | | |
|---|---|---|
| *C07C 31/18* | (2006.01) | |
| *C08G 65/22* | (2006.01) | |
| *C08G 18/50* | (2006.01) | |
| *A01N 31/02* | (2006.01) | |
| *C08G 81/00* | (2006.01) | |
| *C08G 18/75* | (2006.01) | |
| *C09D 175/08* | (2006.01) | |
| *C08G 18/24* | (2006.01) | |
| *C08G 18/48* | (2006.01) | |
| *C08G 18/32* | (2006.01) | |
| *C08K 5/08* | (2006.01) | |
| *C08G 18/64* | (2006.01) | |
| *C11C 3/00* | (2006.01) | |

(52) U.S. Cl.
CPC ..... *C08G 18/3206* (2013.01); *C08G 18/4833* (2013.01); *C08G 18/5015* (2013.01); *C08G 18/758* (2013.01); *C08G 65/226* (2013.01); *C08G 81/00* (2013.01); *C08K 5/08* (2013.01); *C09D 175/08* (2013.01); *C08G 18/6423* (2013.01); *C11C 3/00* (2013.01)

(56) References Cited

U.S. PATENT DOCUMENTS

| | | | |
|---|---|---|---|
| 3,847,978 | A | 11/1974 | Sianesi et al. |
| 4,777,224 | A | 10/1988 | Gorzynski et al. |
| 4,956,438 | A | 9/1990 | Ruetman et al. |
| 5,032,666 | A | 7/1991 | Hu et al. |
| 5,084,315 | A | 1/1992 | Karimi et al. |
| 5,189,135 | A | 2/1993 | Cozzi et al. |
| 5,290,418 | A | 3/1994 | Menchen et al. |
| 5,332,798 | A | 7/1994 | Ferreri et al. |
| 5,589,552 | A | 12/1996 | Simeone et al. |
| 5,798,415 | A | 8/1998 | Corpart et al. |
| 6,071,564 | A | 6/2000 | Marchetti et al. |
| 6,579,835 | B2 | 6/2003 | Scicchitano et al. |
| 6,926,937 | B2 | 8/2005 | Extrand et al. |
| 6,992,132 | B2 | 1/2006 | Trombetta et al. |
| 7,655,310 | B2 | 2/2010 | Trombetta |
| 8,221,847 | B2 * | 7/2012 | Carter .................. B64D 15/08 252/70 |
| 9,136,562 | B2 | 9/2015 | Singh et al. |
| 2002/0016267 | A1 | 2/2002 | Scicchitano et al. |
| 2003/0229176 | A1 | 12/2003 | Trombetta et al. |
| 2004/0019143 | A1 | 1/2004 | Koloski et al. |
| 2005/0164010 | A1 | 7/2005 | Trombetta |
| 2006/0189750 | A1 | 8/2006 | Maier et al. |
| 2007/0298216 | A1 | 12/2007 | Jing et al. |
| 2008/0219944 | A1 | 9/2008 | Longo et al. |
| 2010/0324205 | A1 | 12/2010 | Maier et al. |
| 2011/0177987 | A1 | 7/2011 | Lenting et al. |
| 2011/0218290 | A1 | 9/2011 | Webster et al. |
| 2011/0229750 | A1 | 9/2011 | McLellan et al. |
| 2011/0213085 | A1 | 11/2011 | Tonelli et al. |
| 2012/0136120 | A1 | 2/2012 | Bosman |
| 2012/0164565 | A1 | 6/2012 | Qiu |
| 2014/0113144 | A1 | 4/2014 | Loth et al. |
| 2014/0127516 | A1 | 5/2014 | Wang et al. |
| 2014/0162022 | A1 | 6/2014 | Nowak et al. |
| 2015/0152270 | A1 * | 6/2015 | Aizenberg ............ A61L 29/085 210/500.27 |
| 2015/0158969 | A1 | 6/2015 | Nowak |
| 2015/0329453 | A1 | 11/2015 | Guarda et al. |
| 2016/0009971 | A1 * | 1/2016 | Wang .................. C08G 18/246 428/314.4 |
| 2016/0028114 | A1 | 1/2016 | Pratt et al. |
| 2016/0201005 | A1 | 7/2016 | Nowak et al. |

OTHER PUBLICATIONS

Ashish Vaidya and Manoj K. Chaudhury, "Synthesis and Surface Properties of Environmentally Responsive Segmented Polyurethanes," Journal of Colloid and Interface Science 249, 235-245 (2002).

Siochi et al., "Engineered Surfaces for Mitigation of Insect Residue Adhesion" NF1676L-15481 SAMPE 2013; May 6-9, 2013; Long Beach, CA; United States.

Wohl et al., "Evaluation of commercially available materials to mitigate insect residue adhesion on wing leading edge surfaces," Progress in Organic Coatings 76 (2013) 42-50.

Kok et al., "Influence of surface characteristics on insect residue adhesion to aircraft leading edge surfaces," Progress in Organic Coatings 76 (2013) 1567-1575.

Lee et al, "Zwitter-Wettability and Antifogging Coatings with Frost-Resisting Capabilities," ACS Nano 7 (2013) 2172-2185.

Chen et al., "Robust Prototypical Anti-icing Coatings with a Self-lubricating Liquid Water Layer between Ice and Substrate," ACS Appl. Mater. Interfaces 5 (2013) 4026-4030.

Turri et al., "Waterborne Anionomeric Polyurethane-Ureas from Functionalized Fluoropolyethers," Journal of Applied Polymer Science, vol. 93, 136-144 (2004).

Dou et al., "Anti-icing Coating with an Aqueous Lubricating Layer," ACS Appl. Mater. Interfaces 2014, 6, 6998-7003.

Wang et al., "Investigation of the role of hydrophilic chain length in amphiphilic perfluoropolyether/poly(ethylene glycol) networks: towards high-performance antifouling coatings," Biofouling vol. 27, No. 10, Nov. 2011, 1139-1150.

Chen et al., "A Thermally Re-mendable Cross-Linked Polymeric Material," Science 295 (5560), 1698-1702, Mar. 1, 2002.

Oster et al., "Photoreduction of Metal Ions by Visible Light," Departmenotf Chemistry, Polytechnic Institute of Brooklyn, 135th National meeting of the American Chemical Society, Nov. 5, 1959.

Wojtecki et al., "Using the dynamic bond to access macroscopically responsive structurally dynamic polymers," Nature Materials vol. 10, Jan. 2011.

* cited by examiner 310   320

410  420

510  520

BUGPHOBIC AND ICEPHOBIC COMPOSITIONS WITH LIQUID ADDITIVES

PRIORITY DATA

This patent application claims priority to U.S. Provisional Patent App. No. 62/408,280, filed on Oct. 14, 2016, which is hereby incorporated by reference herein. This patent application is also a continuation-in-part of U.S. patent application Ser. No. 14/829,640, filed on Aug. 19, 2015, which is hereby incorporated by reference herein.

FIELD OF THE INVENTION

The present invention generally relates to structured coatings and compositions suitable for such coatings.

BACKGROUND OF THE INVENTION

Coatings and materials can become soiled from debris (particles, insects, oils, etc.) impacting the surface. The debris affects airflow over the surface as well as aesthetics and normally is removed by washing. Insect impact residue affects vehicle fuel economy, aesthetics, and operator vision. On aircraft, insect residue interferes with airflow over a surface, increasing drag and thus fuel consumption. On automobiles, the light dispersion of headlights, operator vision through the windshield, and aesthetic appeal are degraded from insect remains.

Many solutions to reduce insect debris, such as mechanical scrapers, sacrificial continually released liquid layers, and passive coatings with engineered topology have been flight tested. However, the best-performing liquid layer release systems add a large size and weight penalty while the durability of nanostructured surfaces on aircraft or automobile surfaces is unproven. Attempts to mitigate insect accumulation during the early days of aircraft development included mechanical scrapers, deflectors, traps, in-flight detachable surfaces, in-flight dissolvable surfaces, viscous surface fluids, continuous washing fluids, and suction slots. The results of most of these trials were determined ineffective or impractical for commercial use.

One approach to this problem is to create a passive, self-cleaning surface that removes debris from itself by controlling chemical interactions between the debris and the surface. Passive coatings that reduce insect debris are desirable because they have less parasitic mass and do not require the wiring and energy of active systems. No commercial coating provides sufficient residue reduction.

There has been work at NASA to create anti-insect adhesion or "bugphobic" surfaces; see Wohl et al., "Evaluation of commercially available materials to mitigate insect residue adhesion on wing leading edge surfaces," *Progress in Organic Coatings* 76 (2013) 42-50. Wohl et al. tested the effect of organic-based coatings on insect adhesion to surfaces, but the coatings did not fully mitigate the issue. Wohl et al. also describe previously used approaches to reduce bug adhesion such as mechanical scrapers, deflectors, paper and/or other coverings, elastic surfaces, soluble films, and washing the surface continually with fluid.

Superhydrophobic and superoleophobic surfaces create very high contact angles(>150° between the surface and drops of water and oil, respectively. The high contact angles result in the drops rolling off the surface rather than remaining on the surface. These surfaces do not repel solid foreign matter or vapors of contaminants. Once soiled by impact, debris will remain on the surface and render it ineffective. Also, these surfaces lose function if the nanostructured top surface is scratched.

Enzyme-filled coatings leech out enzymes that dissolve debris on the surface. However, enzymes are quickly depleted and cannot be refilled, rendering this approach impractical.

Kok et al., "Influence of surface characteristics on insect residue adhesion to aircraft leading edge surfaces," *Progress in Organic Coatings* 76 (2013) 1567-1575, describe various polymer, sol-gel, and superhydrophobic coatings tested for reduced insect adhesion after impact. The best-performing materials were high-roughness, superhydrophobic surfaces. However, they did not show that debris could be removed from the superhydrophobic surfaces once insects broke on the surface.

Polymeric materials having low surface energies are widely used for non-stick coatings. These materials are tailored with careful control of their chemical composition (thus surface energy) and mechanical properties. Polymers containing low-energy perfluoropolyethers and perfluoroalkyl groups have been explored for low adhesion and solvent repellency applications. While these low-energy polymers facilitate release of materials adhering to them in both air and water, they do not necessarily provide a lubricated surface to promote clearance of foreign substances. See Vaidya and Chaudhury, "Synthesis and Surface Properties of Environmentally Responsive Segmented Polyurethanes," *Journal of Colloid and Interface Science* 249, 235-245 (2002). A fluorinated polyurethane is described in U.S. Pat. No. 5,332,798 issued Jul. 26, 1994 to Ferreri et al.

Fluoropolymer sheets or treated surfaces have low surface energies and thus low adhesion force between foreign matter and the surface. However, friction between impacting debris and the surface results in the sticking of contaminants.

Fluorofluid-filled surfaces have low adhesion between impacting debris and the surface. However, if any of the fluid is lost, the surface cannot be refilled/renewed once applied on the vehicle, and thus loses its properties (see Wong et al., "Bioinspired self-repairing slippery surfaces with pressure-stable omniphobicity," *Nature* 477, 443-447, 2011). The additional maintenance is highly impractical with real-world automobile and aerospace vehicles.

Coatings and materials can also become contaminated from ice forming on the surface. The debris and ice both affect airflow over the surface, for example. Passive, durable anti-icing coatings have been identified as a need in the aerospace field for many decades. However, previous solutions lacked a required level of performance in ice adhesion reduction, adequate long-term durability, or both of these. Some of the most-effective coatings for reducing ice adhesion are dependent on sacrificial oils or greases that have limited useful lifetimes and require regular reapplication. Currently, durable coatings for exposed areas on fixed wing and rotorcraft (such as the leading edge of the wing or rotorblade) include thermoplastic elastomers bonded to the vehicle surface using a film adhesive or an activated adhesive backing incorporated into the coating itself. However, the prior compositions do not provide any benefit in lowering ice adhesion.

There remains a desire for coatings on aircraft exteriors (and other aerospace-relevant surfaces) in order to passively suppress the growth of ice, in addition to removing debris, near strategic points on the vehicle—such as the rotorblade edge, wing leading edge, or engine inlet. There also exists a need for high-performance coating materials fabricated in a way that preserves coating function during actual use of aerospace structures.

Low-adhesion coatings are useful in both bugphobic and icephobic applications. Low-adhesion coatings are certainly not limited to aerospace-relevant surfaces. Other potential applications include wind turbine blades, automobiles, trucks, trains, ocean-going vessels, electrical power transmission lines, buildings, windows, antennas, filters, instruments, sensors, cameras, satellites, weapon systems, and chemical plant infrastructure (e.g., distillation columns and heat exchangers).

SUMMARY OF THE INVENTION

Some variations of the invention provide a composition comprising: a first solid material and a second solid material that are chemically distinct, wherein the first solid material and the second solid material are microphase-separated on a microphase-separation length scale from about 0.1 microns to about 500 microns, and wherein the first solid material and the second solid material have different surface energies; and at least one liquid selectively absorbed into either of the first solid material or the second solid material.

In some embodiments, the liquid is a freezing-point depressant for water. For example, the liquid may be selected from the group consisting of methanol, ethanol, isopropanol, ethylene glycol, propylene glycol, glycerol, poly(ethylene glycol), and combinations, isomers, or homologous species thereof.

In some embodiments, the liquid is a lubricant. For example, the liquid may be selected from the group consisting of fluorinated oils, fluorocarbon ether polymers of polyhexafluoropropylene, siloxanes, petroleum-derived oils, mineral oil, plant-derived oils, canola oil, soybean oil, and combinations thereof. Alternatively, or additionally, the liquid may contain a solid lubricant suspended or dissolved in the liquid.

In certain embodiments, the liquid is or includes water.

In some embodiments, the liquid is an electrolyte, which may be aqueous or non-aqueous. For example, the liquid may be selected from the group consisting of poly(ethylene glycol), ionic liquids, dimethyl carbonate, diethyl carbonate, methyl ethyl dicarbonate, and combinations thereof.

The liquid may be present in the composition at a concentration from about 5 wt % to about 50 wt %, for example.

In some embodiments, a first liquid is selectively absorbed into either of the first solid material or the second solid material, and the composition further comprises an additional (second) liquid selectively absorbed into the other of the first solid material or the second solid material that does not contain the first liquid.

Prior to incorporation of a liquid, the composition may be regarded as a precursor composition. Some embodiments of the invention provide a precursor composition comprising: a first solid material and a second solid material that are chemically distinct, wherein the first solid material and the second solid material are microphase-separated on a microphase-separation length scale from about 0.1 microns to about 500 microns, and wherein the first solid material and the second solid material have different surface energies.

The microphase-separation length scale is from about 0.5 microns to about 100 microns, in some embodiments. The composition may also be characterized by hierarchical phase separation, in certain embodiments. For example, the first solid material and the second solid material may be nanophase-separated on a nanophase-separation length scale from about 10 nanometers to about 100 nanometers, wherein the nanophase-separation length scale is hierarchically distinct from the microphase-separation length scale.

One of the first solid material and the second solid material may be present as a plurality of discrete inclusions dispersed within a continuous matrix comprising the other of the first solid material and the second solid material.

In some embodiments, one of the first solid material and the second solid material is hydrophobic, and the other of the first solid material and the second solid material is hydrophilic or hygroscopic.

In some embodiments, one of the first solid material and the second solid material has a surface energy from about 5 mJ/m$^2$ to about 50 mJ/m$^2$. The first solid material or the second solid material may be or include a fluoropolymer.

The first solid material and the second solid material are preferably both present as phase-separated regions of a copolymer, such as in a segmented copolymer. An exemplary segmented copolymer is a urethane-urea copolymer.

In certain embodiments of the invention, the first solid material and the second solid material are present as phase-separated regions of a segmented copolymer that includes:

(a) one or more first soft segments selected from fluoropolymers having an average molecular weight from about 500 g/mol to about 20,000 g/mol, wherein the fluoropolymers are $(\alpha,\omega)$-hydroxyl-terminated and/or $(\alpha,\omega)$-amine-terminated;

(b) one or more second soft segments selected from polyesters or polyethers, wherein the polyesters or polyethers are $(\alpha,\omega)$-hydroxyl-terminated and/or $(\alpha,\omega)$-amine-terminated;

(c) one or more isocyanate species or a reacted form thereof, possessing an isocyanate functionality of 2 or greater; and (d) one or more polyol or polyamine chain extenders or a reacted form thereof.

In certain embodiments of the invention, the first solid material and the second solid material are present as phase-separated regions of a segmented copolymer that includes:

(a) fluoropolymers having an average molecular weight from about 500 g/mol to about 20,000 g/mol, wherein the fluoropolymers are $(\alpha,\omega)$-hydroxyl-terminated and/or $(\alpha,\omega)$-amine-terminated, and wherein the fluoropolymers are present in the triblock structure:

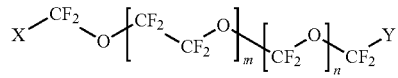

wherein:
X, Y=CH$_2$—(O—CH$_2$—CH$_2$)$_p$-T, and X and Y are independently selected;
p=1 to 50;
T is a hydroxyl or amine terminal group;
m=1 to 100; and
n=1 to 100;

(b) one or more isocyanate species possessing an average isocyanate functionality of about 2 or greater, or a reacted form thereof; and (c) one or more polyol or polyamine chain extenders or crosslinkers optionally possessing an average functionality of about 3 or greater, or a reacted form thereof.

The composition may be present in a coating, such as (but not limited to) an anti-ice coating, an anti-bug coating, and/or an anti-friction coating. The composition may also be present in a layer, an object, or a material. In some embodiments, the composition is present in an energy-transfer material or an energy-storage material.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF EMBODIMENTS OF THE INVENTION

Figure 1:
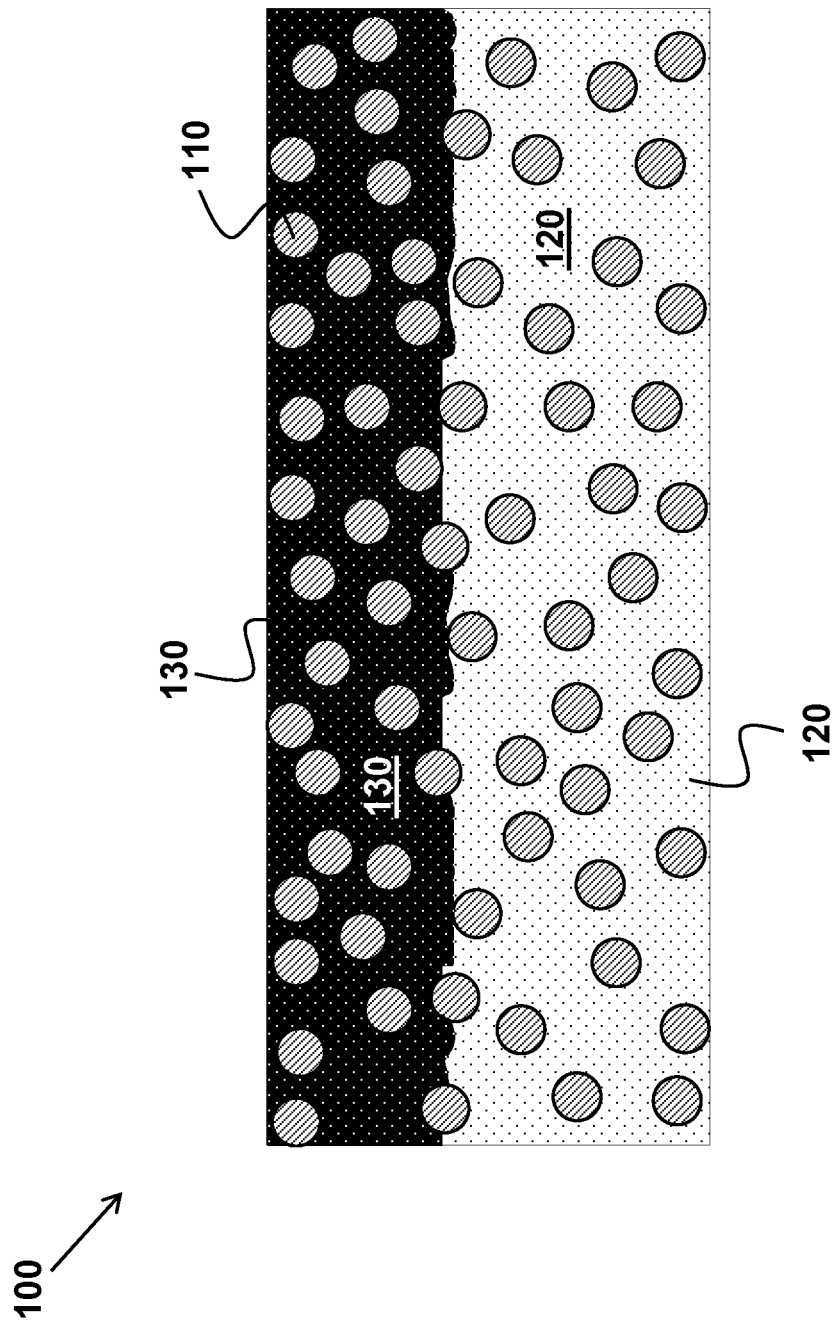
FIG. 1 depicts a composition comprising a first solid material and a second solid material that are microphase-separated, and a liquid selectively absorbed into either of the first solid material or the second solid material, in some embodiments.

The materials, compositions, structures, systems, and methods of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

HRL Laboratories' technologies described in U.S. patent application Ser. No. 14/658,188 (filed on Mar. 14, 2015), U.S. patent application Ser. No. 14/829,640 (filed on Aug. 19, 2015), U.S. patent application Ser. No. 15/073,615 (filed on Mar. 17, 2016), and U.S. patent application Ser. No. 15/608,975 (filed on May 30, 2017) include, among other things, polymeric coating compositions containing fluoropolymer and poly(ethylene glycol) flexible segments that phase-separate to create regions rich in the two respective components on microscopic length scales (such as 0.1-100 μm). These coatings have application potential for bugphobicity due to the fact that they combine non-stick fluoropolymer regions with water-absorbing poly(ethylene glycol) regions that can swell with water and provide lubricity. The combination of non-stick regions and lubrication improves the probability of insects or debris striking the surface and bouncing or sliding off with little to no residue left behind. Certain thermoplastic compositions disclosed in U.S. patent application Ser. No. 14/829,640 have been found to significantly delay the freezing of ice. Certain vulcanized variations disclosed in U.S. patent application Ser. No. 15/073,615 segregate fluoropolymer and water-absorbing elements in discrete block copolymer precursors, for bugphobicity while maintaining good transparency. U.S. patent application Ser. Nos. 14/658,188, 14/829,640, 15/073,615, and 15/608,975 are each hereby incorporated by reference herein.

The concept of a liquid additive introduced to a cross-linked polymer in order to swell the network is well-known. Swelling in crosslinked polymers can be found in common household items such as the polyelectrolytes used in diapers, along with more sophisticated applications including hydrogels in biomedical fields for the growth of cell tissue or drug delivery. Typically, these materials are covalently crosslinked networks composed of a single polymer phase that expands to incorporate liquid with the expansion arrested by the covalent bonding in the network. Multiphase polymeric materials (in particular, block copolymers) have a similar ability to swell in the presence of a liquid. One phase usually swells preferentially, depending on the character of the separate phases and the liquid. With multi-component block copolymers, the nature of the crosslinking that will arrest the swelling can be either covalent, as in the case of vulcanized materials, or physical, as found in many hydrogen-bonded associated structures.

Block copolymers include segmented copolymers containing hard and soft segments. The terminology "hard segments" and "soft segments" derives from the morphology of elastomeric polymers containing phase-separated regions (the hard and soft segments). Generally, soft segments have glass-transition temperatures below 25° C., while hard segments have higher glass-transition temperatures. Soft segments tend to be amorphous, while hard segments are glassy and may be crystalline.

Segmented polyurethanes are one such example of physically associated block copolymers in which the backbone includes statistical segments (i.e., regions of polymer backbone) of flexible, weakly associating soft-segment chains typically between 1,000-5,000 g/mol molecular weight and often composed of polyesters or polyethers mixed with rigid highly associated segments containing a high density of urethane bonds. Such structures normally phase-separate at the molecular level (see Petrovic et al., "POLYURETHANE ELASTOMERS", *Prog. Polym. Sci.*, Vol. 16, 695-836, 1991, which is hereby incorporated by reference herein). The soft segments provide the ability to extend under stress, while the associated hard segments limit flow and creep of the material under stress and provide elastic recovery.

Recently, a class of materials composed of species that are highly dissimilar in their chemical nature, and structured over a surface to express the properties of both individual elements simultaneously, has been reported by HRL Laboratories (Malibu, Calif.). Specific embodiments of these materials have been produced using a segmented polyurethane approach and found to be effective against freezing of ice by combining a low-surface-energy fluorinated species with a hygroscopic freezing-point-depressing component (see U.S. patent application Ser. No. 15/608,975, filed on May 30, 2017, which is hereby incorporated by reference herein). Other embodiments have been created with a covalently crosslinked network to enable decreased build-up of bug material by combining a similar low-surface-energy fluorinated species with lubricating elements that passively absorb moisture from the environment (see U.S. patent application Ser. No. 15/073,615, filed on Mar. 17, 2016, which is hereby incorporated by reference herein).

The technologies disclosed in U.S. patent application Ser. No. 15/073,615 and U.S. patent application Ser. No. 15/608, 975 utilize 100% solid polymer coatings that are microphase-separated at varying length scales. It has now been recognized that there exists the potential to enhance performance further, and/or adjust chemical, physical, or electrical properties of the material, by the addition of a liquid component that favorably interacts with (e.g., swells) a given phase.

This patent application is premised on the preferential incorporation of a liquid additive within one phase of a multiphase polymer coating. The structure of the microphase-separated network provides reservoirs for liquid in either the discrete or continuous phases, or potentially distinct liquids in the different phases. These solid/liquid hybrid materials have potential to improve physical properties associated with the coating in applications such as antifouling (anti-ice and anti-bug), ion conduction, and corrosion resistance. Coating performance may be enhanced compared to coatings containing only solid materials, across a range of applications.

Unless otherwise indicated, all references to "phases" in this patent application are in reference to solid phases. A "phase" is a region of space (a thermodynamic system), throughout which all physical properties of a material are essentially uniform. Examples of physical properties include density and chemical composition. A simple description is that a solid phase is a region of solid material that is chemically uniform and physically distinct from other regions of solid material (or any liquid or vapor materials that may be present). The solid phases are typically polymeric and may melt or at least undergo a glass transition at elevated temperatures. Reference to multiple solid phases in a composition or microstructure means that there are at least two distinct material phases that are solid, without forming a solid solution or homogeneous mixture.

Some variations provide a composition comprising: a first solid material and a second solid material that are chemically distinct, wherein the first solid material and the second solid material are microphase-separated, and wherein the first solid material and the second solid material have different surface energies; and at least one liquid selectively absorbed into either of the first solid material or the second solid material. As intended herein, "microphase-separated" means that the first and second solid materials are physically separated on a microphase-separation length scale from about 0.1 microns to about 500 microns.

By "liquid" it is meant any material that has a liquid phase at 25° C. and 1 bar pressure. Many liquids are possible. One example is water introduced into a hygroscopic phase in order to lubricate the surface to lower potential for debris (e.g., bugs) to accumulate at a surface. Another example is a fluorinated fluid that is incorporated into a low-surface-energy phase to provide a similar lubricating effect. Traditional anti-freeze liquids (such as glycols including ethylene glycol, propylene glycol, glycerol, or polyethylene glycol oligomers) are useful for improving anti-icing properties. The incorporation of carbonate-based liquids or oligomers of polyethers can improve ionic conductivity through a material for use in energy-storage applications, for example.

By "absorbed" it is meant that the liquid is incorporated into the bulk phase of one of the first or second solid materials, and/or onto the surface of one of the first or second solid materials. The absorption is meant to include various mechanisms of chemical or physical incorporation, including but not limited to, chemical or physical absorption, chemical or physical adsorption, chemical bonding, ion exchange, or reactive inclusion (which may convert at least some of the liquid into another component or a different phase). Also an absorbed liquid may or may not be in thermodynamic equilibrium with the local composition or the environment. Absorbed liquids may or may not be permanently contained in the composition; for example, depending on volatility or other factors, some amount of liquid may be lost to the environment over time.

In certain embodiments, the liquid absorption into a given solid material swells that material, which means that there is an increase of volume of that solid material due to absorption of the liquid. Note that the liquid may be, but does not need to be, classified as a solvent for the solid material which it swells. Selectively swelling only one of the solid materials (phases), rather than non-selectively swelling the entire composition, avoids chemically or physically destabilizing the overall polymer network.

By "selectively" absorbed into one of the first or second solid materials, it is meant that of the liquid that absorbs into the composition, at least 51%, preferably at least 75%, and more preferably at least 90% of the liquid absorbs into one of the solid materials. In various embodiments, the selectivity into one of the solid materials can be about, or at least about, 60%, 65%, 70%, 75%, 80%, 85%, 90%, 95%, or 99%. Note that there may be excess liquid that does not absorb into either of the first or second solid materials; this excess liquid can be recovered and is not included in the calculation of selectivity.

The phase-separated microstructure preferably includes discrete islands of one material within a continuous sea of the other material. The continuous or percolating phase(s) provides unbroken channels within the material for transport of mass and/or electrical charge. Either the discrete or continuous phase, or both of these, may serve as a reservoir for performance-enhancing fluids such as anti-freeze liquids, lubricants, or ionic electrolytes. In some embodiments, incorporation of a liquid that is selective for the continuous phase is desirable. In some embodiments, incorporation of a liquid that is selective for the discrete phase is desirable.

In some embodiments, the liquid is a freezing-point depressant for water. For example, the liquid may be selected from the group consisting of methanol, ethanol, isopropanol, ethylene glycol, propylene glycol, glycerol, poly(ethylene glycol), polyols, and combinations, isomers, or homologous species thereof. The freezing-point depressant may be aqueous or non-aqueous.

In some embodiments, the liquid is a lubricant. For example, the liquid may be selected from the group consisting of fluorinated oils, fluorocarbon ether polymers of polyhexafluoropropylene, siloxanes, petroleum-derived oils, mineral oil, plant-derived oils, canola oil, soybean oil, and combinations thereof. The lubricant may be aqueous or non-aqueous.

In certain embodiments, the liquid is or includes water. When it is desired for water to be selectively absorbed into one of the phases, the water may be derived passively from atmospheric humidity, for example. In particular, water absorption may lead to a lubricating surface layer in the presence of humidity.

In some embodiments, the liquid is an electrolyte, which may be aqueous or non-aqueous. For example, the liquid may be selected from the group consisting of poly(ethylene glycol), ionic liquids, dissolved salts, dimethyl carbonate, diethyl carbonate, methyl ethyl dicarbonate, and combinations thereof.

In some embodiments, the composition is present in an energy-transfer material or an energy-storage material. For example, the liquid may be or include electrolytes, ions, salts, active-battery materials (as a liquid, or dissolved or suspended in a liquid), liquid electrodes, catalysts, ionization agents, intercalation agents, and so on.

In some embodiments, a first liquid is selectively absorbed into either of the first solid material or the second solid material, and the composition further comprises an additional (second) liquid selectively absorbed into the other of the first solid material or the second solid material that does not contain the first liquid.

Combinations of liquids are possible. In this case, multiple liquids may be selectively absorbed into one of the first or second solid materials. Alternatively, or additionally, a first liquid may be selectively absorbed into one of the first or second solid materials, and a second liquid may be selectively absorbed into the second or first (i.e., the other) solid material. For example, a first liquid may be an organic material that selectively swells the first solid material, and a second liquid may be water that is selectively absorbed into the second solid material (e.g., a hygroscopic phase). The first liquid could be, for example, mineral oil to improve lubricity and bugphobicity. As another example, a first liquid could electrical or ionic conductivity in a continuous phase (first solid material), while a second liquid adjusts lubrication or water freezing properties of a second solid material.

The liquid, or combination of multiple liquids, may be present in the composition at a concentration from about 5 wt % to about 50 wt %, for example. In various embodiments, the liquid, or combination of multiple liquids, is present in the composition at a concentration of about 1 wt %, 2 wt %, 5 wt %, 10 wt %, 20 wt %, 30 wt %, 40 wt %, 50 wt %, or more.

The liquid may be introduced into one of the phases actively, passively, or a combination thereof. In some embodiments, a liquid is actively introduced to a phase by spraying of the liquid, deposition from a vapor phase containing the liquid material, liquid injection, liquid bath immersion, or other techniques. In some embodiments, a liquid is passively introduced to a phase by letting a liquid naturally be extracted from the normal atmosphere, or from a local atmosphere adjusted to contain one or more desired liquids in vapor or droplet (e.g., mist) form.

In certain embodiments, the desired additive is normally a solid at room temperature and is first dissolved or suspended in a liquid that is then absorbed into the first or second material of the composition.

In other certain embodiments, the desired additive is normally a solid at room temperature and is first melted to produce a liquid that is then absorbed into the first or second material of the composition. Within the composition, the desired additive may partially or completely solidify back to a solid, or may form a multiphase material, for example. Thus in certain embodiments, the composition includes at least one additive selectively absorbed into either of the first solid material or the second solid material, wherein the additive may be derived from a solid, liquid, or vapor, and wherein the additive, when present in the composition, may be in liquid, solid, or liquid-solid solution form.

Optionally, the liquid may contain solid particles (solid at a temperature of 25° C. and 1 bar pressure) suspended or dissolved in the liquid. For example, the liquid may contain solid lubricant particles suspended or dissolved in the liquid. A "solid lubricant" reduces friction of an object or particle that is sliding along the surface of a coating containing the material. A solid lubricant aids the sliding of debris (e.g., bug fragments, dirt, ice, etc.) across the surface. Exemplary solid lubricants include graphite and molybdenum disulfide. Solid particles may be included in the liquid for other reasons, such as for coating strength or durability, or to enhance absorption of the liquid into the selected phase, for example.

In other embodiments, the liquid may contain solid particles that function as a freezing-point depressant, wherein the solid particles are suspended or dissolved in the liquid which may then be drawn into the polymer. For example, polyols (e.g., pentaerythritol, dipentaerythritol, or tripentaerythritol) may be dissolved in a solvent, such as methanol, ethanol, glycerol, ethylene glycol, formamide, or water, and then absorbed into the first or second solid material. The high density of OH groups in polyols may be beneficial to disrupt crystallization of water. When solid polyols are employed, they may be melted into the polymer structure, followed by solidification of the polyols within the first or second solid material of the composition.

One of the first solid material and the second solid material may be present as a plurality of discrete inclusions dispersed within a continuous matrix comprising the other of the first solid material and the second solid material.

In some embodiments, one of the first solid material and the second solid material is hydrophobic, and the other is hydrophilic or hygroscopic. In certain embodiments, a continuous matrix (first solid material) is hygroscopic or further includes a hygroscopic material. In these or other embodiments, discrete inclusions (second solid material) are hygroscopic or further include a hygroscopic material.

As intended in this patent application, "hygroscopic" means that the material is capable of attracting and holding water molecules from the surrounding environment. The water uptake of various polymers is described in Thijs et al., "Water uptake of hydrophilic polymers determined by a thermal gravimetric analyzer with a controlled humidity chamber", J. Mater. Chem. (17) 2007, 4864-4871, which is hereby incorporated by reference herein. In some embodiments, the hygroscopic material is characterized by a water absorption capacity, at 90% relative humidity and 30° C., of at least 5, 10, 15, 20, 25, 30, 35, 40, 45, or 50 wt % increase due to water uptake.

In some embodiments, one of the first solid material and second solid material is oleophobic, and the other is oleophilic.

In some embodiments, one of the first solid material and the second solid material may be a "low-surface-energy polymer" which means a polymer, or a polymer-containing material, with a surface energy of no greater than 50 mJ/m$^2$. In some embodiments, one of the first solid material and the second solid material has a surface energy from about 5 mJ/m$^2$ to about 50 mJ/m$^2$.

The first solid material or the second solid material may be or include a fluoropolymer, such as (but not limited to) a fluoropolymer selected from the group consisting of polyfluoroethers, perfluoropolyethers, fluoroacrylates, fluorosilicones, polytetrafluoroethylene (PTFE), polyvinylidene difluoride (PVDF), polyvinylfluoride (PVF), polychlorotrifluoroethylene (PCTFE), copolymers of ethylene and trifluoroethylene, copolymers of ethylene and chlorotrifluoroethylene, and combinations thereof.

In these or other embodiments, the first solid material or the second solid material may be or include a siloxane. A siloxane contains at least one Si—O—Si linkage. The siloxane may consist of polymerized siloxanes or polysiloxanes (also known as silicones). One example is polydimethylsiloxane.

In some embodiments, the first solid material is a continuous matrix and the second solid material is a plurality of discrete inclusions. In other embodiments, the first solid material is a plurality of discrete inclusions and the second solid material is a continuous matrix. The discrete inclusions may be different phases (microphase-separated regions) of a common material such as a segmented copolymer. Alternatively, or additionally, the discrete inclusions may be another material entirely, such as nanoparticles. In some embodiments, there are both phase-separated inclusions of the same chemical material, as well as physically and chemically distinct materials as additional inclusions.

The first solid material and the second solid material are optionally both present as phase-separated regions of a copolymer, such as a block copolymer. As intended herein, a "block copolymer" means a copolymer containing a linear arrangement of blocks, where each block is defined as a portion of a polymer molecule in which the monomeric units have at least one constitutional or configurational feature absent from the adjacent portions. Several types of block copolymers are generally possible, including AB block copolymers, ABA block copolymers, ABC block copolymers, segmented block copolymers, and random copolymers. Segmented block copolymers are preferred, in some embodiments of the invention.

In some preferred embodiments, a segmented block copolymer provides two (or more) phases. A liquid is selected to absorb selectively into one of the phases, or potentially in two phases when there are three or more phases present, or generally in less than all of the phases present in the composition. An exemplary segmented copolymer is a urethane-urea copolymer.

In certain embodiments of the invention, the first solid material and the second solid material are present as phase-separated regions of a segmented copolymer that includes:

(a) one or more first soft segments selected from fluoropolymers having an average molecular weight from about 500 g/mol to about 20,000 g/mol, wherein the fluoropolymers are ($\alpha,\omega$)-hydroxyl-terminated and/or ($\alpha,\omega$)-amine-terminated;

(b) one or more second soft segments selected from polyesters or polyethers, wherein the polyesters or polyethers are ($\alpha,\omega$)-hydroxyl-terminated and/or ($\alpha,\omega$)-amine-terminated;

(c) one or more isocyanate species or a reacted form thereof, possessing an isocyanate functionality of 2 or greater; and (d) one or more polyol or polyamine chain extenders or a reacted form thereof.

It is noted that ($\alpha,\omega$)-terminated polymers are terminated at each end of the polymer. The $\alpha$-termination may be the same or different than the $\omega$-termination. Also it is noted that in this disclosure, "($\alpha,\omega$)-termination" includes branching at the ends, so that the number of terminations may be greater than 2 per polymer molecule. The polymers herein may be linear or branched, and there may be various terminations and functional groups within the polymer chain, besides the end ($\alpha,\omega$) terminations.

In some embodiments, the molar ratio of the second soft segments to the first soft segments is from about 0.1 to about 1.5. In various embodiments, the molar ratio of the second soft segments to the first soft segments is about 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 1.95.

In this description, "polyurethane" is a polymer comprising a chain of organic units joined by carbamate (urethane) links, where "urethane" refers to N(H)—(C=O)—O—. Polyurethanes are generally produced by reacting an isocyanate containing two or more isocyanate groups per molecule with one or more polyols containing on average two or more hydroxyl groups per molecule, in the presence of a catalyst.

Polyols are polymers in their own right and have on average two or more hydroxyl groups per molecule. For example, $\alpha,\omega$-hydroxyl-terminated perfluoropolyether is a type of polyol.

"Isocyanate" is the functional group with the formula —N=C=O. For the purposes of this disclosure, O—C(=O)—N(H)—R is considered a derivative of isocyanate. "Isocyanate functionality" refers to the number of isocyanate reactive sites on a molecule. For example, diisocyanates have two isocyanate reactive sites and therefore a isocyanate functionality of 2. Triisocyanates have three isocyanate reactive sites and therefore a isocyanate functionality of 3.

"Polyfluoroether" refers to a class of polymers that contain an ether group—an oxygen atom connected to two alkyl or aryl groups, where at least one hydrogen atom is replaced by a fluorine atom in an alkyl or aryl group.

"Perfluoropolyether" (PFPE) is a highly fluorinated subset of polyfluoroethers, wherein all hydrogen atoms are replaced by fluorine atoms in the alkyl or aryl groups.

"Polyurea" is a polymer comprising a chain of organic units joined by urea links, where "urea" refers to N(H)—(C=O)—N(H)—. Polyureas are generally produced by reacting an isocyanate containing two or more isocyanate groups per molecule with one or more multifunctional amines (e.g., diamines) containing on average two or more amine groups per molecule, optionally in the presence of a catalyst.

A "chain extender or crosslinker" is a compound (or mixture of compounds) that link long molecules together and thereby complete a polymer reaction. Chain extenders or crosslinkers are also known as curing agents, curatives, or hardeners. In polyurethane/urea systems, a curative is typically comprised of hydroxyl-terminated or amine-terminated compounds which react with isocyanate groups present in the mixture. Diols as curatives form urethane linkages, while diamines as curatives form urea linkages. The choice of chain extender or crosslinker may be determined by end groups present on a given prepolymer. In the case of isocyanate end groups, curing can be accomplished through chain extension using multifunctional amines or alcohols, for example. Chain extenders or crosslinkers can have an average functionality greater than 2 (such as 2.5, 3.0, or greater), i.e. beyond diols or diamines.

In some embodiments, the polyesters or polyethers are selected from the group consisting of poly(oxymethylene), poly(ethylene glycol), poly(propylene glycol), poly(tetrahydrofuran), poly(glycolic acid), poly(caprolactone), poly(ethylene adipate), poly(hydroxybutyrate), poly(hydroxyalkanoate), and combinations thereof.

In some embodiments, the isocyanate species is selected from the group consisting of 4,4'-methylenebis(cyclohexyl isocyanate), hexamethylene diisocyanate, cycloalkyl-based diisocyanates, tolylene-2,4-diisocyanate, 4,4'-methylenebis(phenyl isocyanate), isophorone diisocyanate, and combinations or derivatives thereof.

The polyol or polyamine chain extender or crosslinker possesses a functionality of 2 or greater, in some embodiments. At least one polyol or polyamine chain extender or crosslinker may be selected from the group consisting of 1,4-butanediol, 1,3-propanediol, 1,2-ethanediol, glycerol, trimethylolpropane, ethylenediamine, isophoronediamine, diaminocyclohexane, and homologues, derivatives, or combinations thereof. In some embodiments, polymeric forms of polyol chain extenders or crosslinkers are utilized, typically hydrocarbon or acrylic backbones with hydroxyl groups distributed along the side groups. These crosslinkers may possess a functionality of greater than 2, such as 3 or more.

The one or more chain extenders or crosslinkers (or reaction products thereof) may be present in a concentration, in the segmented copolymer composition, from about 0.01 wt % to about 25 wt %, such as about 0.05 wt % to about 10 wt %.

In certain embodiments of the invention, the first solid material and the second solid material are present as phase-separated regions of a segmented copolymer that includes:

(a) fluoropolymers having an average molecular weight from about 500 g/mol to about 20,000 g/mol, wherein the fluoropolymers are (α,ω)-hydroxyl-terminated and/or (α,ω)-amine-terminated, and wherein the fluoropolymers are present in the triblock structure:

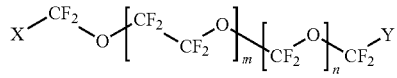

wherein:
X, Y=CH$_2$—(O—CH$_2$—CH$_2$)$_p$-T, and X and Y are independently selected;
p=1 to 50;
T is a hydroxyl or amine terminal group;
m=1 to 100; and
n=1 to 100;

(b) one or more isocyanate species possessing an average isocyanate functionality of about 2 or greater, or a reacted form thereof; and (c) one or more polyol or polyamine chain extenders or crosslinkers optionally possessing an average functionality of about 3 or greater, or a reacted form thereof.

The composition may be present in a coating, such as (but not limited to) an anti-ice coating, an anti-bug coating, and/or an anti-friction coating. The composition may also be present in a layer, an object, or a material.

For example, a first solid material and a chemically distinct second solid material may be combined structurally at a coating surface to create discrete domains or islands that are microphase-separated on a microphase-separation length scale from about 0.1 microns to about 500 microns. The two distinct species are designed or selected such that one is oleophobic and the other is oleophilic. The liquid that selectively absorbs into either of the first solid material or the second solid material may be oil or an oil-containing liquid, which selectively absorbs into the oleophilic phase. Such a coating has applications in oil clean-up, smudge resistance, among others.

An oleophilic material has a strong affinity for oils. As meant herein, the term "oleophilic" means a material with a contact angle of hexadecane (model oil compound) of 90° or less. An oleophilic material may also be classified as lipophilic. An oleophobic material has a poor affinity for oils. As intended herein, the term "oleophobic" means a material with a contact angle of hexadecane greater than 90°. An oleophobic material may also be classified as lipophobic.

In some embodiments, a segmented polyurethane includes a microphase-separated structure of fluorinated and hydrocarbon species. Segmented copolymers are typically created by combining a flexible oligomeric soft segment terminated with an alcohol or amine reactive groups and a multifunctional isocyanate. When the isocyanate is provided in excess relative to the alcohol/amine reactive groups, a viscous prepolymer mixture with a known chain length distribution is formed. This can then be cured to a high-molecular-weight network through the addition of amine or alcohol reactive groups to bring the ratio of isocyanate to amine/alcohol groups to unity. The product of this reaction is a chain backbone with alternating segments: soft segments of flexible oligomers and hard segments of the reaction product of low-molecular-weight isocyanates and alcohol/amines.

Due to the chemical immiscibility of these two phases, the material typically phase-separates on the length scale of these individual molecular blocks, thereby creating a microstructure of flexible regions adjacent to rigid segments strongly associated through hydrogen bonding of the urethane/urea moieties. This combination of flexible and associated elements typically produces a physically crosslinked elastomeric material.

It is also possible to incorporate two or more soft-segment oligomer blocks into a segmented polyurethane system, wherein the separate oligomer block tends to phase-separate on the molecular scale. This can result in more complex microstructures. Depending on relative composition of the two soft segments, discrete or continuous phases may result.

In these or other embodiments, a fluorinated continuous matrix is coupled with hydrocarbon-coated inorganic nanoparticles dispersed within the matrix. A segmented copolymer may be synthesized, with the addition of only one highly fluorinated soft-segment oligomer. Combining the functionalized oligomer with isocyanate and alcohol curatives creates a microphase-separated matrix, wherein the fluorinated oligomer forms a continuous network. Functionalized nanoparticles (e.g., silica nanoparticles) may be added to the reaction mixture prior to curing. Other nanoparticles include, but are not limited to, alumina, titanium dioxide, and iron oxide.

In these or other embodiments, fluorinated polyurethane oligomers are terminated with silane groups. The end groups on the oligomers (in the prepolymer) may be modified from isocyanate to silyl ethers. This can be accomplished through reaction of an isocyanate-reactive silane species (e.g., aminopropyltriethoxysilane) to provide hydrolysable groups well-known in silicon and siloxane chemistry. Such an approach eliminates the need for addition of a stoichiometric amount of curative to form strongly associative hard segments, while replacing the curative with species that possess the ability to form a covalently crosslinked network under the influence of moisture or heat. Such chemistry has been shown to preserve beneficial aspects of urethane coatings while boosting scratch resistance.

In addition, the reactivity of the terminal silane groups allows for additional functionality in the form of complimentary silanes blended with the prepolymer mixture. The silanes are able to condense into the hydrolysable network upon curing. This strategy allows for discrete domains of distinct composition. A specific embodiment relevant to anti-fouling involves the combination of fluoro-containing urethane prepolymer that is endcapped by silane reactive groups with additional alkyl silanes.

In certain embodiments incorporating oleophilic and oleophobic phases, the first solid material and the second solid material are present as phase-separated regions of a segmented copolymer that includes:

(a) one or more first soft segments selected from fluoropolymers having an average molecular weight from about 500 g/mol to about 20,000 g/mol, wherein said fluoropolymers are ($\alpha,\omega$)-hydroxyl-terminated and/or ($\alpha,\omega$)-amine-terminated;

(b) one or more second soft segments selected from saturated or unsaturated polymeric hydrocarbons that are ($\alpha,\omega$)-hydroxyl-terminated and/or ($\alpha,\omega$)-amine-terminated;

(c) one or more isocyanate species, or a reacted form thereof, possessing an isocyanate functionality of 2 or greater; and (d) one or more polyol or polyamine chain extenders or crosslinkers, or a reacted form thereof.

The oleophilic material may be organic or inorganic. In some embodiments, the oleophilic material is a polymer, such as a polyolefin, which may be selected from the group consisting of polyethylene, polypropylene, polybutene, polybutadiene, polymethylpentene, polyisobutylene, polyisoprene, and combinations thereof. In some embodiments, the oleophilic material is a carbonaceous material, such as graphene, graphene oxides, or carbon aerogels.

In some embodiments, the oleophilic material is an inorganic material that is surface-modified to contain a hydrocarbon surface species, such as a hydrocarbon surface species selected from the group consisting of saturated or unsaturated $C_6$-$C_{20}$ hydrocarbon groups (e.g., alkyl or aryl groups such as octyl, decyl, or octadecyl groups, or homologues thereof).

The oleophilic material may be an inorganic material derived from a hydrolysable silane, such as octyltrimethoxysilane, octyltriethoxysilane, decyltrimethyoxysilane, decyltriethyoxysilane, octadecyltrimethoxysilane, octadecyltriethoxysilane, or combinations or homologues thereof.

In some embodiments, the oleophobic material has a surface energy from about 5 mJ/m² to about 50 mJ/m². The oleophobic material may be selected from the group consisting of perfluoropolyethers, polytetrafluoroethylene, polyvinylidene fluoride, polyvinyl fluoride, perfluoroethers, fluoroacrylates, fluorosilicones, siloxanes, and combinations thereof.

The first solid material (e.g., discrete inclusions) may be present in a concentration from about 5 wt % to about 95 wt % based on total weight of the composition. In various embodiments, the first solid material may be present in a concentration of about 5, 10, 20, 30, 40, 50, 60, 70, 80, 90, or 95 wt % based on total weight of the composition.

The second solid material (e.g., continuous matrix) may be present in a concentration from about 5 wt % to about 95 wt % based on total weight of the composition. In various embodiments, the second solid material may be present in a concentration of about 5, 10, 20, 30, 40, 50, 60, 70, 80, 90, or 95 wt % based on total weight of the composition.

The absorbed liquid or liquids may be present in a concentration from about 0.01 wt % to about 50 wt % (or more) based on total weight of the composition. In various embodiments, the absorbed liquid or liquids may be present in a concentration of about 0.1, 0.5, 1, 2, 5, 10, 20, 30, 40, or 50 wt % based on total weight of the composition.

In addition to the first and second solid materials and the absorbed liquid(s), various solid additives may be present. Additives may be selected from the group consisting of a particulate filler, a pigment, a dye, a plasticizer, a flame retardant, a flattening agent, and a substrate adhesion promoter.

The microphase-separated microstructure containing the first and second solid materials may be characterized as an inhomogeneous microstructure. As intended in this patent application, "phase inhomogeneity," "inhomogeneous microstructure," and the like mean that a multiphase microstructure is present in which there are at least two discrete phases that are separated from each other. The two phases may be one discrete solid phase in a continuous solid phase, two $\omega$-continuous solid phases, or two discrete solid phases in a third continuous solid phase, for example. The length scale of phase inhomogeneity may refer to the average size (e.g., effective diameter) of discrete inclusions of one phase dispersed in a continuous phase. The length scale of phase inhomogeneity may refer to the average center-to-center distance between nearest-neighbor inclusions of the same phase. The length scale of phase inhomogeneity may alternatively refer to the average separation distance between nearest-neighbor regions of the discrete (e.g., droplets) phase, where the distance traverses the continuous phase.

The average length scale of phase inhomogeneity may generally be from about 0.1 microns to about 500 microns, which in this disclosure is also generally referred to as "microphase separation." In some embodiments, the average length scale of phase inhomogeneity is from about 0.5 microns to about 100 microns, such as about 1 micron to about 50 microns. In various embodiments, the average length scale of phase inhomogeneity is about 0.1, 0.2, 0.3, 0.4, 0.5, 0.6, 0.7, 0.8, 0.9, 1, 2, 3, 4, 5, 10, 15, 20, 25, 30, 35, 40, 45, 50, 60, 70, 80, 90, 100, 150, 200, 250, 300, 350, 400, 450, or 500 microns, including any intermediate values not explicitly recited, and ranges starting, ending, or encompassing such intermediate values. These are average values, noting that a portion of phase inhomogeneity may be present on a length scale less than 0.1 micron or greater than 500 microns (e.g., about 1000 microns), with the overall average falling in the range of 0.1-500 microns. (Note that in this disclosure, "about 0.1 microns" is intended to encompass 50-149 nanometers, i.e. ordinary rounding.)

This phase inhomogeneity typically causes opaque coatings or films due to the scattering of light. Scattering of light including visible wavelengths in the bulk of a material is governed by changes in the index of refraction through the medium. Variations in refractive index at length scales near the wavelength of the propagating radiation will tend to scatter those wavelengths more effectively (Mie scattering), resulting in an opaque or white appearance for a coating. With visible light having a wavelength range of about 400-700 nm, a clear or transparent coating must typically keep variations in index of refraction below about 50 nm in length. As phase inhomogeneities increase in length scale, the opacity of the material rises. Phase inhomogeneities with average length scale from 0.1 µm to 500 µm are expected to drive significant scattering in the material, leading to opaque structures above 25 µm in thickness—unless the multiple phases happen to be refractive index-matched. See Althues et al., "Functional inorganic nanofillers for transparent polymers", Chem. Soc. Rev., 2007, 36, 1454-1465, which is hereby incorporated by reference herein for its teaching that materials with inhomogeneity below 50 nm will tend to be clear, and materials with inhomogeneity above 50 nm (0.05 µm) will tend to be more opaque.

In preferred embodiments, the first solid material and second solid material are microphase-separated on a length scale from about 0.1 microns to about 500 microns. Therefore, these compositions tend to be non-transparent—unless there happens to be refractive index matching of the first solid material and second solid material (and absorbed liquid when in a significant concentration). In some embodiments, the composition is opaque with respect to ordinary light. In certain embodiments, the composition is semi-transparent or transparent with respect to ordinary light.

The composition may also be characterized by hierarchical phase separation. For example, the first solid material and the second solid material, in addition to being microphase-separated, are typically nanophase-separated. As intended herein, two materials being "nanophase-separated" means that the two materials are separated from each other on a length scale from about 1 nanometer to about 100 nanometers. For example, the nanophase-separation length scale may be from about 10 nanometers to about 100 nanometers.

The nanophase-separation length scale is hierarchically distinct from the microphase-separation length scale. With traditional phase separation in block copolymers, the blocks chemically segregate at the molecular level, resulting in regions of segregation on the length scale of the molecules, such as a nanophase-separation length scale from about 10 nanometers to about 100 nanometers. Again see Petrovic et al., "POLYURETHANE ELASTOMERS", Prog. Polym. Sci., Vol. 16, 695-836, 1991. The extreme difference of the two soft segments means that in the reaction pot the soft segments do not mix homogeneously and so create discrete region that are rich in fluoropolymer or rich in non-fluoropolymer (e.g., PEG) components, distinct from the molecular-level segregation. These emulsion droplets contain a large amount of polymer chains and are thus in the micron length-scale range. These length scales survive the curing process, so that the final material contains the microphase separation that was set-up from the emulsion, in addition to the molecular-level segregation.

In some embodiments, therefore, the larger length scale of separation (0.1-500 microns) is driven by an emulsion process, which provides microphase separation that is in addition to classic molecular-level phase separation. Chen et al., "Structure and morphology of segmented polyurethanes: 2. Influence of reactant incompatibility," POLYMER 1983, Vol. 24, pages 1333-1340, is hereby incorporated by reference herein for its teachings about microphase separation that can arise from an emulsion-based procedure.

In some embodiments, the nanophase-scale separation is on the length scale of microstructure domains that include (1) a fluid-resistant, chemically inert, hydrophobic soft segment; (2) a hygroscopic (water-absorbing) and/or liquid-swellable soft segment; and (3) a rigid, highly associated hard segment that provides network reinforcement and stability. In a composition possessing hierarchical phase separation, a first microphase may contain nanophases of (1) along with nanophases of (3), while a second microphase may contain nanophases of (2) along with nanophases of (3). Without being limited by speculation, it is believed that in the CLSM images of FIGS. 3A, 3B, 4A, 4B, 5A, and 5B, the dark regions are microphases that contain hydrophobic soft segments and highly associated hard segments, each being nanophase-separated; and the light regions are microphases that contain hygroscopic soft segments and highly associated hard segments, also each being nanophase-separated.

In some embodiments, discrete inclusions have an average size (e.g., effective diameter) from about 50 nm to about 150 µm, such as from about 100 nm to about 100 µm. In various embodiments, discrete inclusions have an average size (e.g., effective diameter) of about 50 nm, 100 nm, 200 nm, 500 nm, 1 µm, 2 µm, 5 µm, 10 µm, 50 µm, 100 µm, or 200 µm.

In these or other embodiments, discrete inclusions have an average center-to-center spacing between adjacent inclusions, through a continuous matrix, from about 50 nm to about 150 µm, such as from about 100 nm to about 100 µm. In various embodiments, discrete inclusions have an average center-to-center spacing between adjacent inclusions of about 50 nm, 100 nm, 200 nm, 500 nm, 1 µm, 2 µm, 5 µm, 10 µm, 50 µm, 100 µm, or 200 µm.

The composition may be characterized by a transparency of less than 70% average light transmission in the wavelength range of 400 nm to 700 nm, through a 1-millimeter-thick sample (defined test depth). In some embodiments, the composition transparency is less than about 65%, 60%, 55%, 50%, 45%, 40%, 35%, 30%, 25%, 20%, 15%, or 10% average light transmission in the wavelength range of 400 nm to 700 nm, through a 1-millimeter-thick sample.

In some variations of the invention, the composition forms a coating disposed on a substrate. The coating may have a thickness from about 1 µm to about 10 mm, for example. In various embodiments, the coating thickness is about 100 nm, 1 µm, 10 µm, 100 µm, 1 mm, or 10 mm. Thicker coatings provide the benefit that even after surface abrasion, the coating still functions because the entire depth of the coating (not just the outer surface) contains the first and second solid materials. The coating substrate composition and thickness will depend on the specific application.

Figure 2:
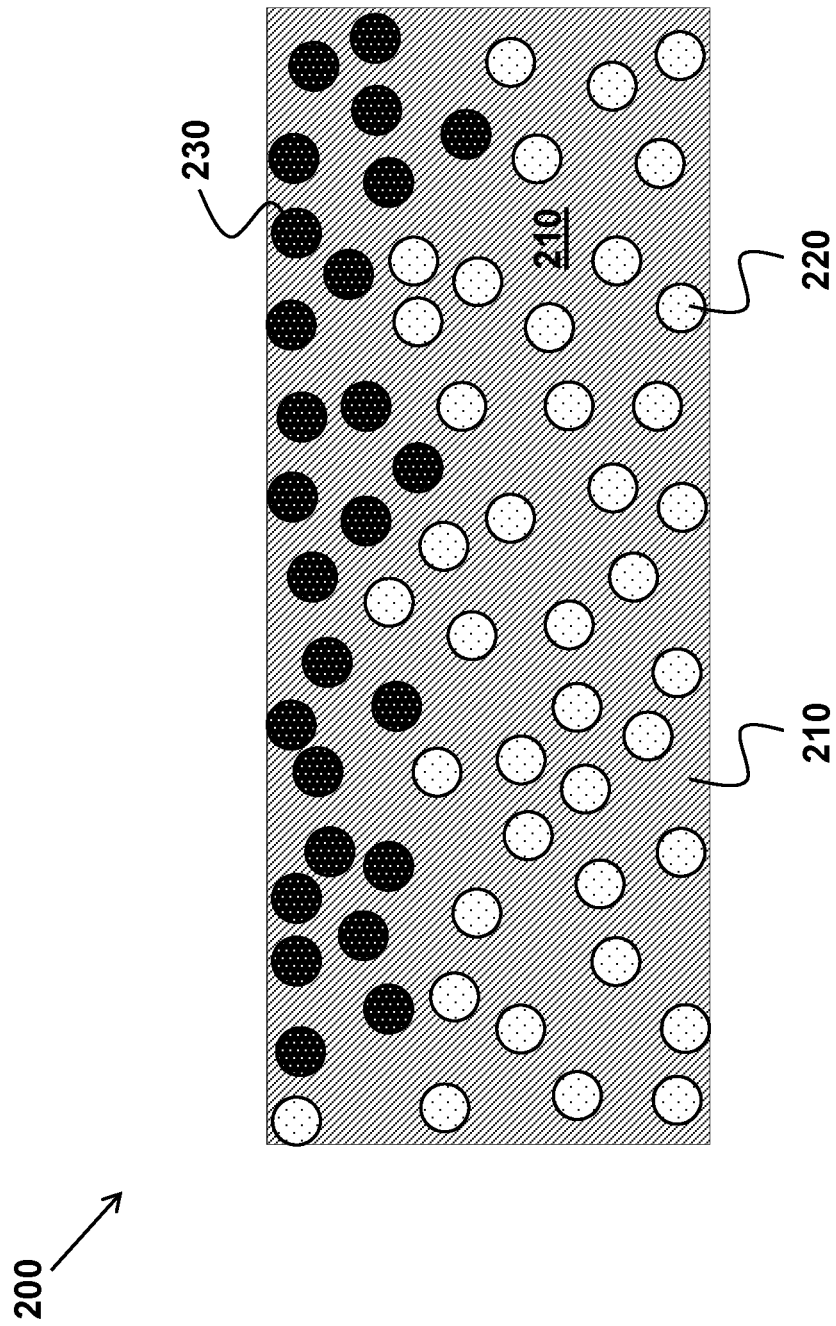
FIG. 2 depicts a composition comprising a first solid material and a second solid material that are microphase-separated, and a liquid selectively absorbed into either of the first solid material or the second solid material, in some embodiments.

Various embodiments and strategies are depicted in the drawings of FIGS. 1 and 2, which should not be construed to limit the invention. These drawings are for illustration purposes and are not to scale. The drawings of FIGS. 1 and 2 are two-dimensional cross-sections, as a side view. The top of each structure represents the surface that is exposed to the environment.

In FIG. 1, the structure 100 includes a continuous matrix 120 and a plurality of discrete inclusions 110 dispersed throughout the continuous matrix 120. While FIG. 1 depicts (for illustration) the discrete inclusions 110 as circles/spheres, this is not meant to imply a limitation. Other geometries of discrete inclusions 110 are possible, including regular or irregular shapes, as well as various sizes and size distributions. The inclusions 110 may vary in size, such as from about 0.1 to 500 microns in diameter or effective diameter. The inclusions 110 may be dispersed uniformly (e.g., ordered) or non-uniformly (e.g., randomly). The number of inclusions 110 per unit volume may vary, such that the inclusions 110 collectively are present in a concentration from about 5 wt % to about 95 wt % based on total weight of the composition, for example.

A liquid 130 is absorbed into a portion of continuous matrix 120, which functions as a reservoir for the absorbed liquid 130 (e.g., water, oil, or liquid electrolyte). In FIG. 1, the continuous matrix absorbs the liquid selectively, compared to any liquid absorption into the discrete inclusions.

FIG. 1 implies that the continuous matrix 120 near the surface has captured liquid 130, while the continuous matrix 120 in the distal region from the surface (e.g., closer to a substrate material) has not captured a significant amount of liquid. This could be due to the fact that the total amount of liquid that has been absorbed is below the maximum capacity of the continuous matrix 120, or because FIG. 1 is a snapshot in time, for example. It should be understood that more liquid may continue to be absorbed into the continuous matrix 120. Also it is noted that the transition between the portion of continuous matrix 120 that contains liquid 130, and the continuous matrix 120 that does not contain liquid, is intentionally depicted as an imperfect line. Due to the nature of the chemical and physical mechanisms involved, a straight line would not be expected, even in the absence of channeling through voids or cracks.

Some variations of the invention are depicted in FIG. 2, which is an alternative configuration compared to FIG. 1. In particular, in FIG. 2, the inclusions absorb the liquid selectively, compared to any liquid absorption into the continuous matrix.

In FIG. 2, the structure 200 includes a continuous matrix 210 and a plurality of discrete inclusions 220 dispersed throughout the continuous matrix 210. While FIG. 2 depicts (for illustration) the discrete inclusions 210 as circles/spheres, this is not meant to imply a limitation. Other geometries of discrete inclusions 210 are possible, including regular or irregular shapes, as well as various sizes and size distributions. The inclusions 210 may vary in size, such as from about 0.1 to 500 microns in diameter or effective diameter. The inclusions 210 may be dispersed uniformly (e.g., ordered) or non-uniformly (e.g., randomly). The number of inclusions 210 per unit volume may vary, such that the inclusions 210 collectively are present in a concentration from about 5 wt % to about 95 wt % based on total weight of the composition, for example.

A liquid is absorbed into a portion of the discrete inclusions 220, which function as reservoirs for the absorbed liquid 230 (e.g., water, oil, or liquid electrolyte).

FIG. 2 implies that most of the discrete inclusions 220 near the surface have captured liquid to therefore become liquid-containing inclusions 230, while the inclusions 220 in the distal region from the surface (e.g., closer to a substrate material) of the continuous matrix 210 have not captured a significant amount of liquid. This could be due to the fact that the total amount of liquid that has been deposited is below the maximum capacity of the plurality of inclusions 220 that are present, or because FIG. 2 is a snapshot in time, for example. It should be understood that more liquid may continue to be absorbed into the inclusions 230.

Besides the absorbed liquid, other liquid contaminants may strike the surface of structure 100 or 200. Solid contaminants such as dust, dirt, or insects may also strike the surface of structure 100 or 200. Vapor contaminants such as oil vapor, water vapor, or smoke may also strike the surface of structure 100 or 200. Depending on the impacting material, the contaminant can become absorbed in the two phases or in one of the phases selectively.

An optional substrate (not shown) may be disposed on the back side of the material, at the bottom of FIGS. 1 and 2. A substrate will be present when the material forms a coating or a portion of a coating (e.g., one layer of a multilayer coating). Many substrates are possible, such as a metal, polymer, or glass substrate. Other layers may be present, within the substrate or on the opposite (relative to the coating) side of the substrate. Such other layers may include, for example, metallic layers, conductive layers, and adhesive layers.

Various strategies to form the materials of FIG. 1 or 2 are possible, as will be appreciated by a skilled artisan.

Prior to incorporation of a liquid, the composition may be regarded as a precursor composition. Some embodiments of the invention provide a precursor composition comprising: a first solid material and a second solid material that are chemically distinct, wherein the first solid material and the second solid material are microphase-separated on a microphase-separation length scale from about 0.1 microns to about 500 microns, and wherein the first solid material and the second solid material have different surface energies.

The precursor composition may be waterborne, solventborne, or a combination thereof. In waterborne embodiments, the first or second solid material may be derived from an aqueous dispersion of a linear crosslinkable polyurethane containing charged groups, and the other solid material may be derived from a crosslinking agent containing charged groups, for example.

Some embodiments employ waterborne polyurethane dispersions combining oleophobic and oleophilic species. Waterborne polyurethane dispersions are desired as low volatile organic compound (VOC) alternatives to traditional coating formulations. A successful waterborne polyurethane dispersion often requires the specific components to contain ionic groups to aid in stabilizing the emulsion. Other factors contributing to the formulation of a stable dispersion include the concentration of ionic groups, concentration of water or solvent, and rate of water addition and mixing during the inversion process. An isocyanate prepolymer may be dispersed in water. Subsequently, a curative component may be dispersed in water. Water evaporation then promotes the formation of a microphase-separated polyurethane material as the precursor composition.

Any known methods to fabricate these materials may be employed. Notably, these materials may utilize synthesis methods that enable simultaneous deposition of components or precursor materials to reduce fabrication cost and time. In particular, these materials may be formed by a one-step process, in some embodiments. In other embodiments, these materials may be formed by a multiple-step process.

The composition or precursor composition may be formed from a precursor material (or combination of materials) that may be provided, obtained, or fabricated from starting components. The precursor material is capable of hardening or curing in some fashion, to form a precursor composition containing the first solid material and second solid material, microphase-separated on a microphase-separation length scale from about 0.1 microns to about 500 microns. The precursor material may be a liquid; a multiphase liquid; a multiphase slurry, emulsion, or suspension; a gel; or a dissolved solid (in solvent), for example.

The first and second solid materials may be in the same phase or in different phases, within the precursor material. In some embodiments, the first solid material is in liquid or dissolved form while the second solid material is in dissolved-solid or suspended solid form. In some embodiments, the first solid material is in dissolved-solid or suspended-solid form while the second solid material is in liquid or dissolved form. In some embodiments, the first and second solid materials are both in liquid form. In some embodiments, the first and second solid materials are both in dissolved form, dissolved with an aqueous or non-aqueous solvent.

In some embodiments of the invention, an emulsion sets up in the reaction mixture based on incompatibility between the two blocks (e.g., PEG and PFPE). The emulsion provides microphase separation in the precursor material. The precursor material is then cured from casting or spraying. The microphase separation survives the curing process (even if the length scales change somewhat during curing), providing the benefits in the final materials (or precursor compositions) as described herein. Without being limited by theory, the microphase separation in this invention is not associated with molecular length-scale separation (5-50 nm) that many classic block-copolymer systems exhibit. Rather, the larger length scales of microphase separation, i.e. 0.1-500 µm, arise from the emulsion that was set-up prior to curing.

Xu et al., "Structure and morphology of segmented polyurethanes: 1. Influence of incompatibility on hard-segment sequence length," POLYMER 1983, Vol. 24, pages 1327-1332 and Chen et al., "Structure and morphology of segmented polyurethanes: 2. Influence of reactant incompatibility," POLYMER 1983, Vol. 24, pages 1333-1340, are each hereby incorporated by reference herein for their teachings about emulsion set-up in polyurethane systems prior to curing.

In some variations of the invention, a precursor material is applied to a substrate and allowed to react, cure, or harden to form a final composition (e.g., coating). In some embodiments, a precursor material is prepared and then dispensed (deposited) over an area of interest. Any known methods to deposit precursor materials may be employed. A fluid precursor material allows for convenient dispensing using spray coating or casting techniques.

The fluid precursor material may be applied to a surface using any coating technique, such as (but not limited to) spray coating, dip coating, doctor-blade coating, air knife coating, curtain coating, single and multilayer slide coating, gap coating, knife-over-roll coating, metering rod (Meyer bar) coating, reverse roll coating, rotary screen coating, extrusion coating, casting, or printing. Because relatively simple coating processes may be employed, rather than lithography or vacuum-based techniques, the fluid precursor material may be rapidly sprayed or cast in thin layers over large areas (such as multiple square meters).

When a solvent or carrier fluid is present in the fluid precursor material, the solvent or carrier fluid may include one or more compounds selected from the group consisting of water, alcohols (such as methanol, ethanol, isopropanol, or tert-butanol), ketones (such as acetone, methyl ethyl ketone, or methyl isobutyl ketone), hydrocarbons (e.g., toluene), acetates (such as tert-butyl acetate), acids (such as organic acids), bases, and any mixtures thereof. When a solvent or carrier fluid is present, it may be in a concentration of from about 10 wt % to about 99 wt % or higher, for example.

The precursor material may be converted to an intermediate material or the final composition using any one or more of curing or other chemical reactions, or separations such as removal of solvent or carrier fluid, monomer, water, or vapor. Curing refers to toughening or hardening of a polymeric material by physical crosslinking, covalent crosslinking, and/or covalent bonding of polymer chains, assisted by electromagnetic waves, electron beams, heat, and/or chemical additives. Chemical removal may be accomplished by heating/flashing, vacuum extraction, solvent extraction, centrifugation, etc. Physical transformations may also be involved to transfer precursor material into a mold, for example. Additives may be introduced during the hardening process, if desired, to adjust pH, stability, density, viscosity, color, or other properties, for functional, ornamental, safety, or other reasons.

The liquid (to be incorporated selectively into the first or second solid material) is typically added after the cured material is produced. Depending on the nature of the liquid, it is possible to add some or all of the liquid to the precursor material, or during curing, for example.

Periodic replenishment of liquids into the composition may be desired. For example, some or all of the liquid could eventually go away by various mechanisms including vaporization (as discussed above), solubility into environmental conditions, reaction, and so on. When additional liquid is desired, it may be introduced into one of the phases actively, passively, or a combination thereof. In some embodiments, additional liquid is actively introduced to a phase by spraying of the liquid, deposition from a vapor phase containing the liquid material, liquid injection, liquid bath immersion, or other techniques.

It may also be desirable in certain situations to remove some or all of a liquid from the first or second solid material. Depending on the nature of the liquid, it may be removed by vaporization (e.g., by heating), gas injection to sweep out the liquid, extraction with another material (e.g., a solvent for the liquid), or a chemical reaction, for example.

EXAMPLES

Materials.

Poly(ethylene glycol) with $M_n$=3,400 g/mol (PEG), 4,4'-methylenebis (cyclohexyl isocyanate) (HMDI), 1,4-butanediol (BD), and dibutyltin dilaurate (DBTDL) are purchased from Sigma Aldrich. Fluorolink D4000 and E10H are purchased from Solvay Specialty Polymers.

Example 1: Preparation of Segmented Copolymer (75% PEG Content) with Microphase-Separated Regions PEG (1.5 mmoles, 5.0 g) and HMDI (9.8 mmoles, 2.57 g) are added into a 3-neck flask equipped with a mechanical stirrer. The reaction flask is placed in a 100° C. oil bath and the reaction is carried out under argon. Once PEG is melted and dissolved in the HMDI, 2 µL of DBTDL is added to the mix. The reaction mixture is stirred at 100° C. for 1 hour. Fluorolink D4000 (0.5 mmoles, 2 g) is added and stirring is continued for another 1 hour. The reaction flask is removed from the 100° C. oil bath, and allowed to cool down before adding THF (10 mL) and BD (7.8 mmoles, 0.71 g) dissolved in THF (2 mL). The sample is sprayed with an airbrush using a 0.5-mm needle nozzle aperture to a thickness of 1-5 mils on aluminum, glass, and Mylar® (biaxially-oriented polyethylene terephthalate).

The polymer network is composed of both a water-absorbing (hydrophilic) and a water-repelling (hydrophobic) material. To investigate the film's network and microphase separation of the opposing materials, confocal microscopy is employed. Confocal microscopy is an optical imaging technique that detects fluorescence by exposing the specimen to light of a certain wavelength to excite fluorescent dyes. Samples are prepared by soaking a thin slice of film in an aqueous solution containing fluorescein (10 to 100 µM), a water-soluble dye, for 24 hours. Water absorbed by the film contains fluorescein, allowing contrast between the hydrophilic and hydrophobic domains. Once removed from the solution, the film is rinsed with DI water to remove excess fluorescein from the surface. The film is quickly pat dried to remove water droplets and placed on a glass slide (75×25 mm). A glass coverslip (0.17 mm thick) is placed firmly on the film and the edges are sealed with a quick cure 5-minute epoxy. The edges are sealed to prevent evaporation of water to allow optimal imaging of the specimen by better matching the refractive index of the glass. The fluorescent imaging is obtained using a Leica SP 5 confocal microscope with an argon laser for an excitation wavelength at 496 nm for fluorescein, giving an emission at 512 nm in water.

Figure 3A:
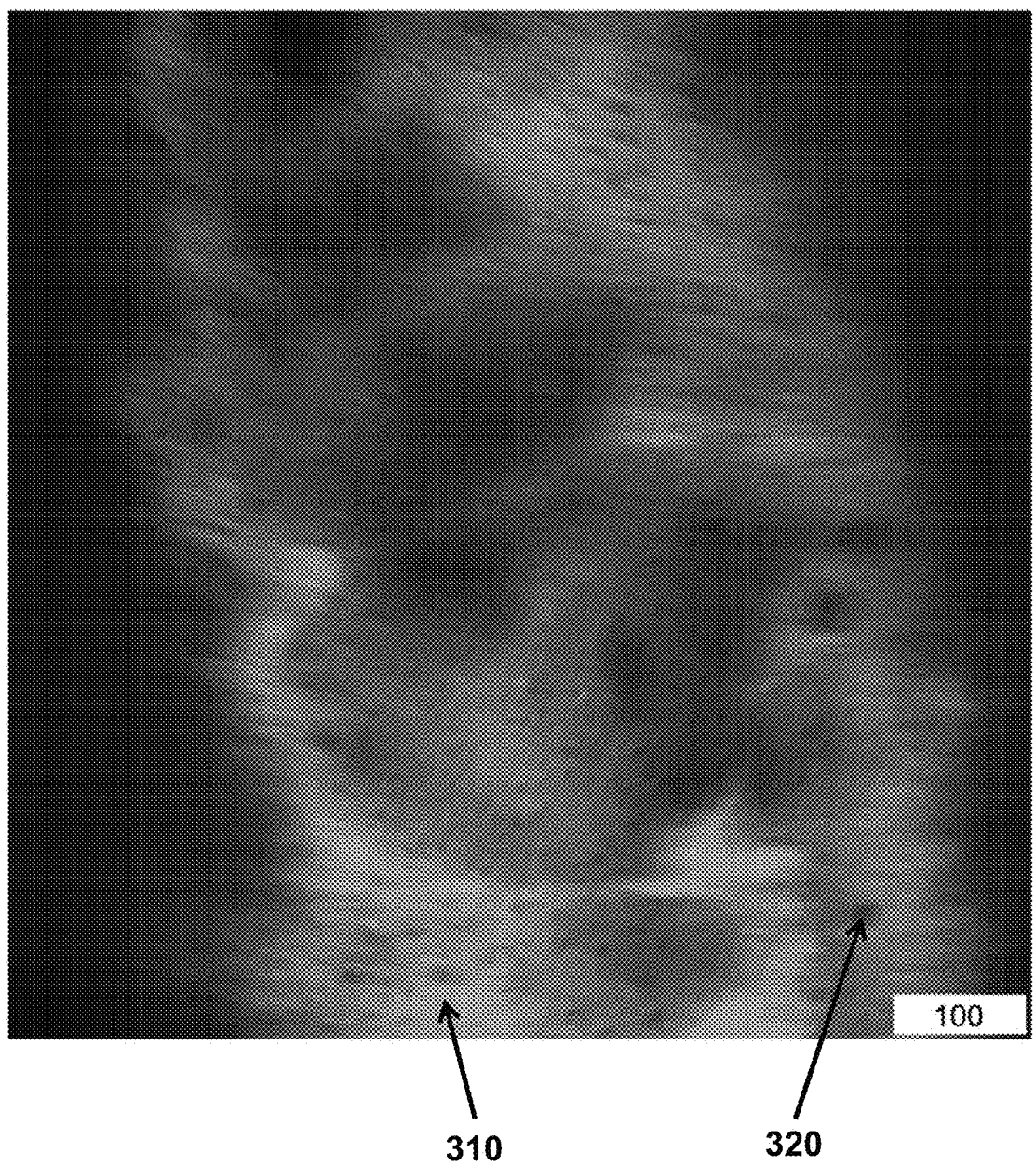
FIG. 3A is a confocal laser scanning microscopy image for the polymer film of Example 1 (scale bar=100 μm).
Figure 3B:
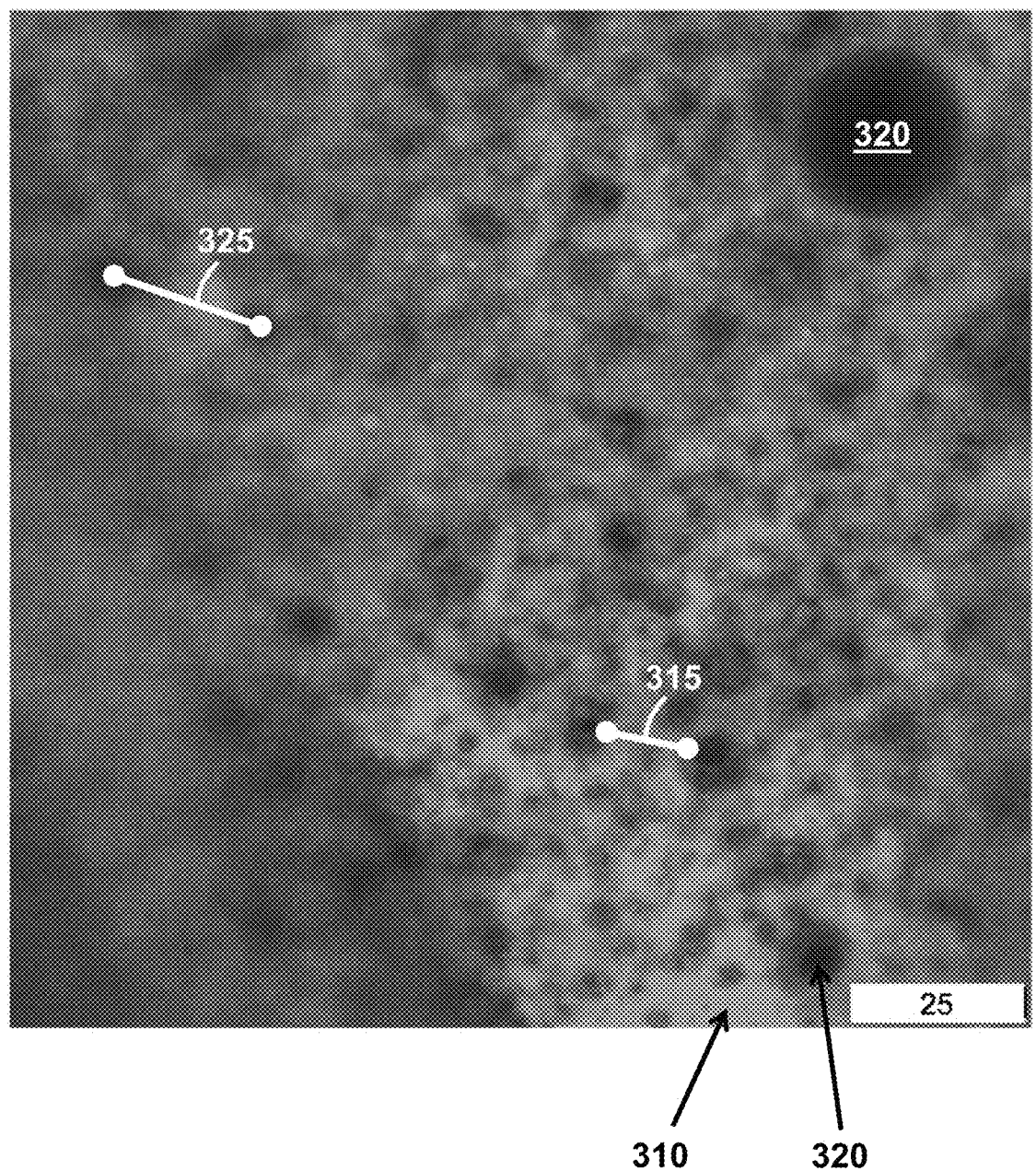
FIG. 3B is a confocal laser scanning microscopy image for the polymer film of Example 1 (scale bar=25 μm).

FIGS. 3A and 3B show confocal laser scanning microscopy (CLSM) images for the polymer film with 75 mol % PEG content. CLSM images are shown at different magnifications of the Example 1 films soaked with water-soluble fluorescent dye.

The fluorescent regions 310 (which display as green regions in the color drawings and lighter regions when reproduced in grayscale) are representative of hydrophilic PEG regions containing a water-soluble fluorescent dye. The inclusions 320 (which display as darker regions) are representative of hydrophobic fluoropolymer regions. The scale bars are 100 µm and 25 µm in FIGS. 3A and 3B, respectively.

Microphase separation is shown in these images. The length scale of phase inhomogeneity for the structure in FIGS. 3A and 3B appears to be in the range of 1 to 100 microns. In particular, the phase inhomogeneity can be characterized by a length scale associated with a discrete phase 320. For example, the length scale of phase inhomogeneity may refer to the average size (e.g., effective diameter) of discrete inclusions of one phase 320 dispersed in a continuous phase 310. The selected (for illustration) inclusions 320 labeled in FIG. 3B have an effective diameter of about 10-20 microns; generally the inclusions have an effective diameter of about 1 to 100 microns in FIGS. 3A and 3B. The length scale of phase inhomogeneity may refer to the average center-to-center distance 325 between nearest-neighbor inclusions of the same phase 320. In FIG. 3B, the selected center-to-center distance 325 is about 25 microns. The length scale of phase inhomogeneity may alternatively refer to the average separation distance 315 between nearest-neighbor regions of the discrete (e.g., droplets) phase 320, i.e. the size of the continuous phase 310 regions. In FIG. 3B, the selected separation distance 315 is about 15 microns. A range of particle sizes and separations is clearly present in this structure; the specific instances of features 310, 315, 320, and 325 were arbitrarily selected.

As described earlier, emulsified droplets rich in either PEG or PFPE are sprayed or cast from a mixture. Upon addition of a curative and the evaporation of a solvent, these droplets coalesce to form a continuous film that is inhomogeneous on the microscale (1-100 µm). In FIGS. 3A and 3B, the dark PFPE-rich areas form a discrete phase (320) that is hydrophobic in character, while the dyed PEG-rich regions form a continuous phase (310) surrounding the discrete regions.

Example 2: Preparation of Segmented Copolymer (50% PEG Content) with Microphase-Separated Regions PEG (1.1 mmoles, 3.83 g) and HMDI (11.2 mmoles, 2.95 g) are added into a 3-neck flask equipped with a mechanical stirrer. The reaction flask is placed in a 100° C. oil bath and the reaction is carried out under argon. Once PEG is melted and dissolved in the HMDI, 2.3 µL of DBTDL is added to the mix. The reaction mixture is stirred at 100° C. for 1 hour. Fluorolink D4000 (1.1 mmoles, 4.5 g) is added and stirring is continued for another 1 hour. The reaction flask is removed from the 100° C. oil bath, and allowed to cool down before adding THF (10 mL) and BD (9.0 mmoles, 0.81 g) dissolved in THF (2 mL). The sample is sprayed with an airbrush using a 0.5-mm needle nozzle aperture to a thickness of 1-5 mils on aluminum, glass and Mylar® (biaxially-oriented polyethylene terephthalate).

Figure 4A:
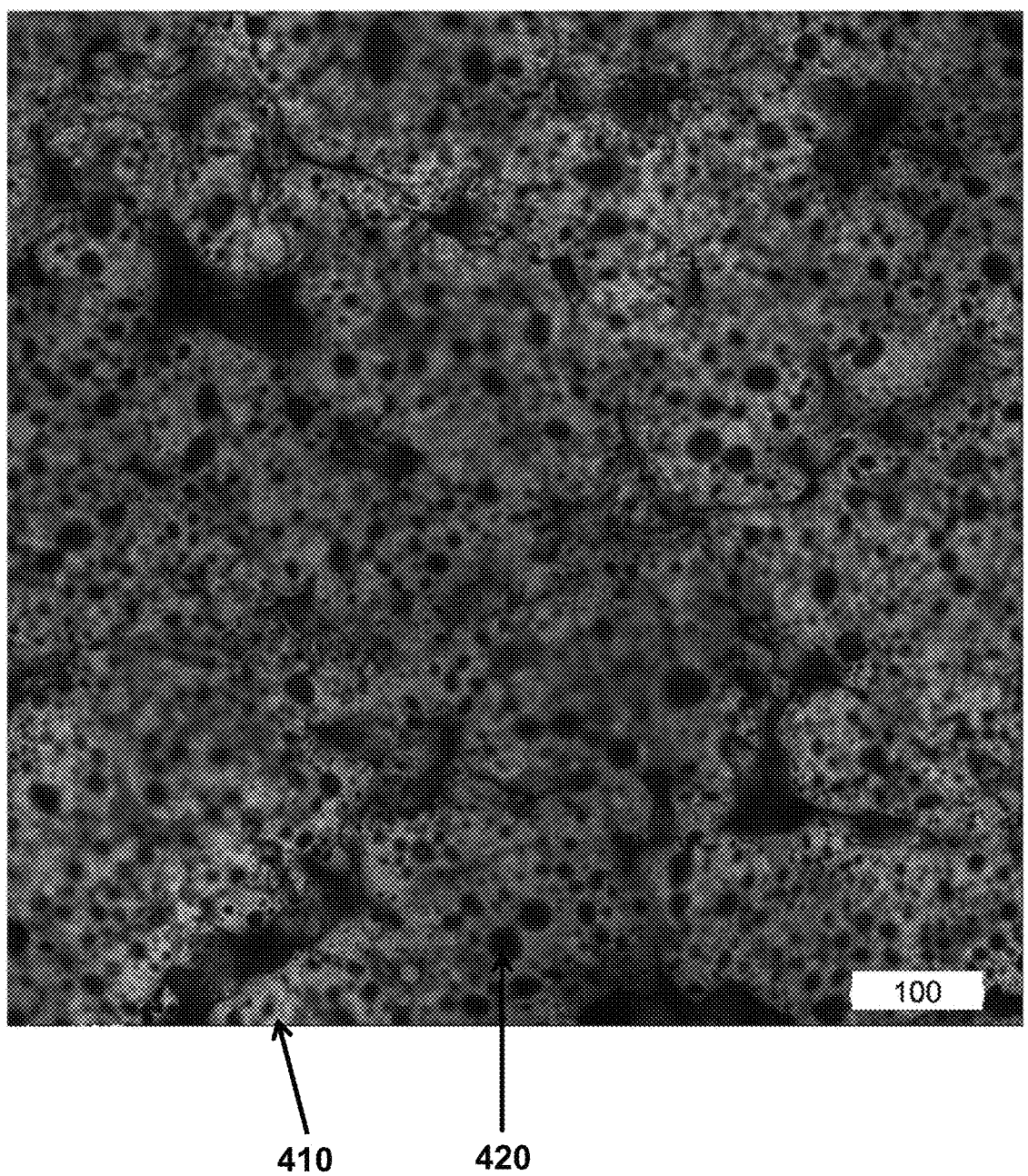
FIG. 4A is a confocal laser scanning microscopy image for the polymer film of Example 3 (scale bar=100 μm).
Figure 4B:
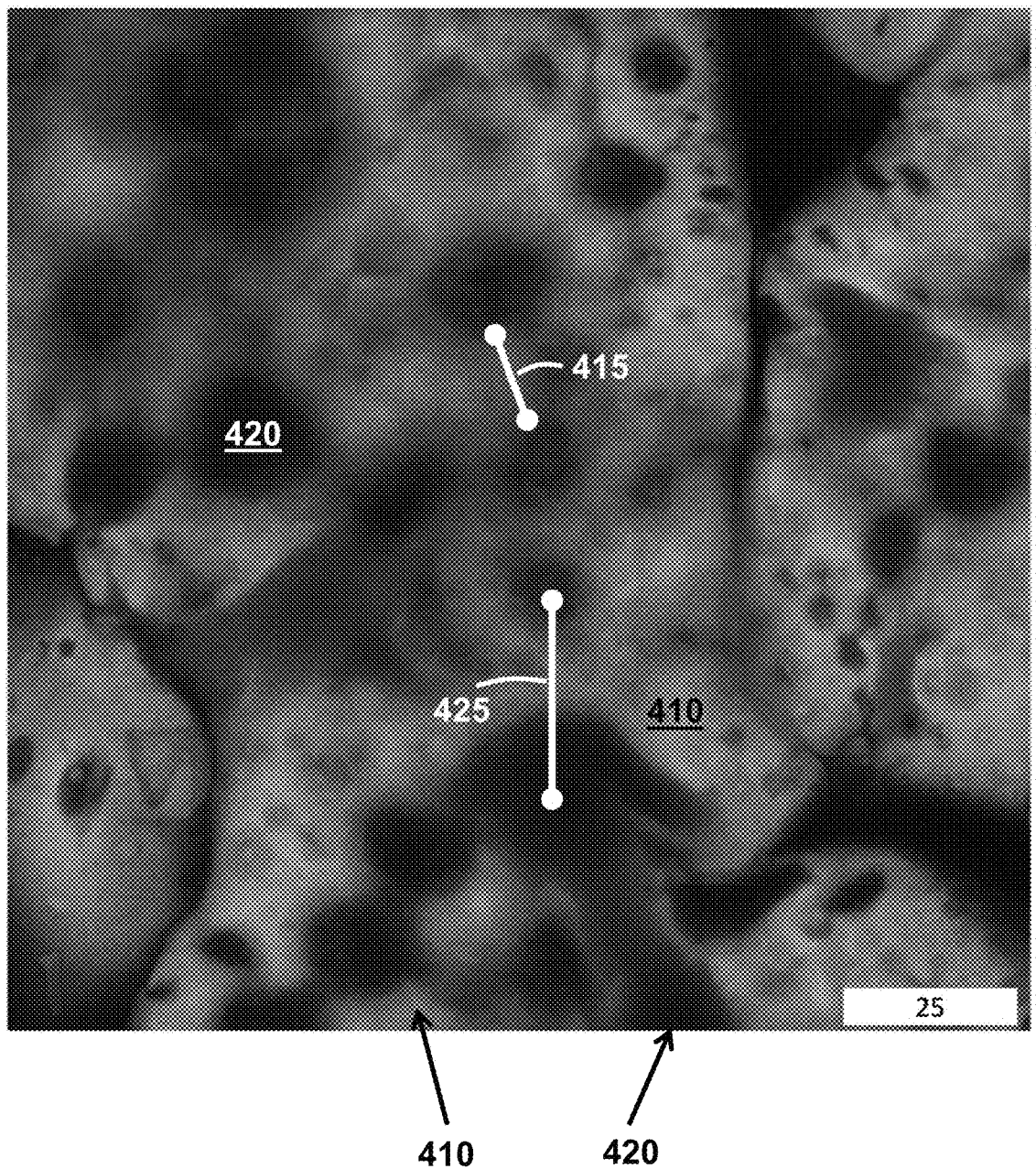
FIG. 4B is a confocal laser scanning microscopy image for the polymer film of Example 3 (scale bar=25 μm).

Confocal microscopy is again employed, using the same procedure as described in Example 1. FIGS. 4A and 4B show confocal laser scanning microscopy (CLSM) images for the polymer film with 50 mol % PEG content. CLSM images are shown at different magnifications of the Example 2 films soaked with water-soluble fluorescent dye.

The fluorescent regions 410 (which display as green regions in the color drawings and lighter regions when reproduced in grayscale) are representative of hydrophilic PEG regions containing a water-soluble fluorescent dye. The inclusions 420 (which display as darker regions) are representative of hydrophobic fluoropolymer regions. The scale bars are 100 µm and 25 µm in FIGS. 4A and 4B, respectively.

Microphase separation is shown in these images. The length scale of phase inhomogeneity for the structure in FIGS. 4A and 4B appears to be in the range of 1 to 100 microns. In particular, the phase inhomogeneity can be characterized by a length scale associated with a discrete phase 420. For example, the length scale of phase inhomogeneity may refer to the average size (e.g., effective diameter) of discrete inclusions of one phase 420 dispersed in a continuous phase 410. The selected (for illustration) inclusions 420 labeled in FIG. 4B have an effective diameter of about 15-20 microns; generally the inclusions have an effective diameter of about 1 to 100 microns in FIGS. 4A and 4B. The length scale of phase inhomogeneity may refer to the average center-to-center distance 425 between nearest-neighbor inclusions of the same phase 420. In FIG. 4B, the selected center-to-center distance 425 is about 30 microns. The length scale of phase inhomogeneity may alternatively refer to the average separation distance 415 between nearest-neighbor regions of the discrete (e.g., droplets) phase 420, i.e. the size of the continuous phase 410 regions. In FIG. 4B, the selected separation distance 415 is about 15 microns. A range of particle sizes and separations is clearly present in this structure; the specific instances of features 410, 415, 420, and 425 were arbitrarily selected.

As described earlier, emulsified droplets rich in either PEG or PFPE are sprayed or cast from a mixture. Upon addition of a curative and the evaporation of a solvent, these droplets coalesce to form a continuous film that is inhomogeneous on the microscale (1-100 μm). In FIGS. 4A and 4B, the dark PFPE-rich areas form a discrete phase (420) that is hydrophobic in character, while the dyed PEG-rich regions form a continuous phase (410) surrounding the discrete regions.

Example 3: Preparation of Segmented Copolymer (25% PEG Content) with Microphase-Separated Regions PEG (0.6 mmoles, 2.0 g) and HMDI (11.8 mmoles, 3.08 g) are added into a 3-neck flask equipped with a mechanical stirrer. The reaction flask is placed in a 100° C. oil bath and the reaction is carried out under argon. Once PEG is melted and dissolved in the HMDI, 2.4 μL of DBTDL is added to the mix. The reaction mixture is stirred at 100° C. for 1 hour. Fluorolink D4000 (1.8 mmoles, 7.06 g) is added and stirring is continued for another 1 hour. The reaction flask is removed from the 100° C. oil bath, and is allowed to cool down before adding THF (10 mL) and BD (9.4 mmoles, 0.85 g) dissolved in THF (2 mL). The sample is sprayed with an airbrush using a 0.5-mm needle nozzle aperture to a thickness of 1-5 mils on aluminum, glass and Mylar® (biaxially-oriented polyethylene terephthalate).

Figure 5A:
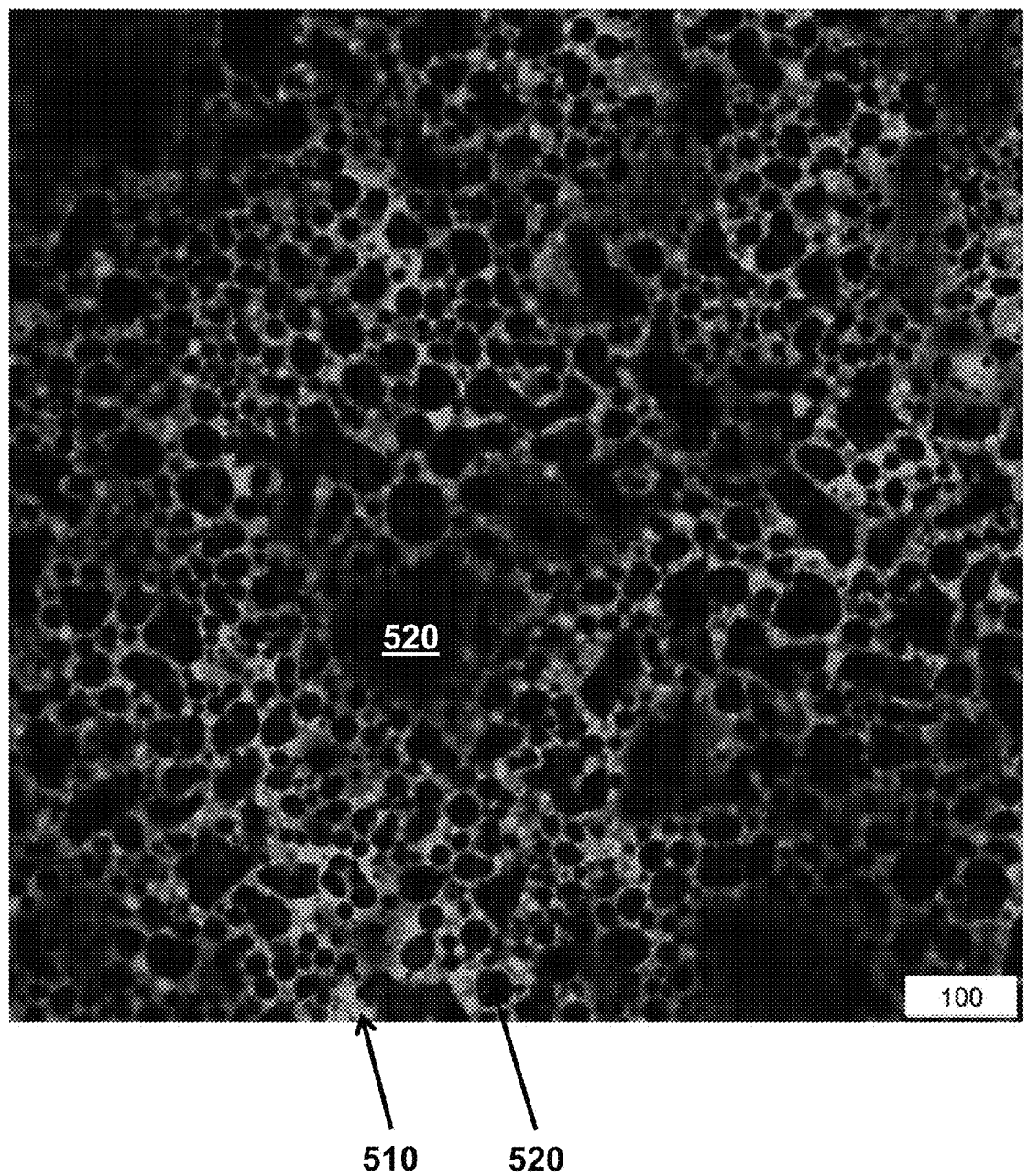
FIG. 5A is a confocal laser scanning microscopy image for the polymer film of Example 1 (scale bar=100 μm).
Figure 5B:
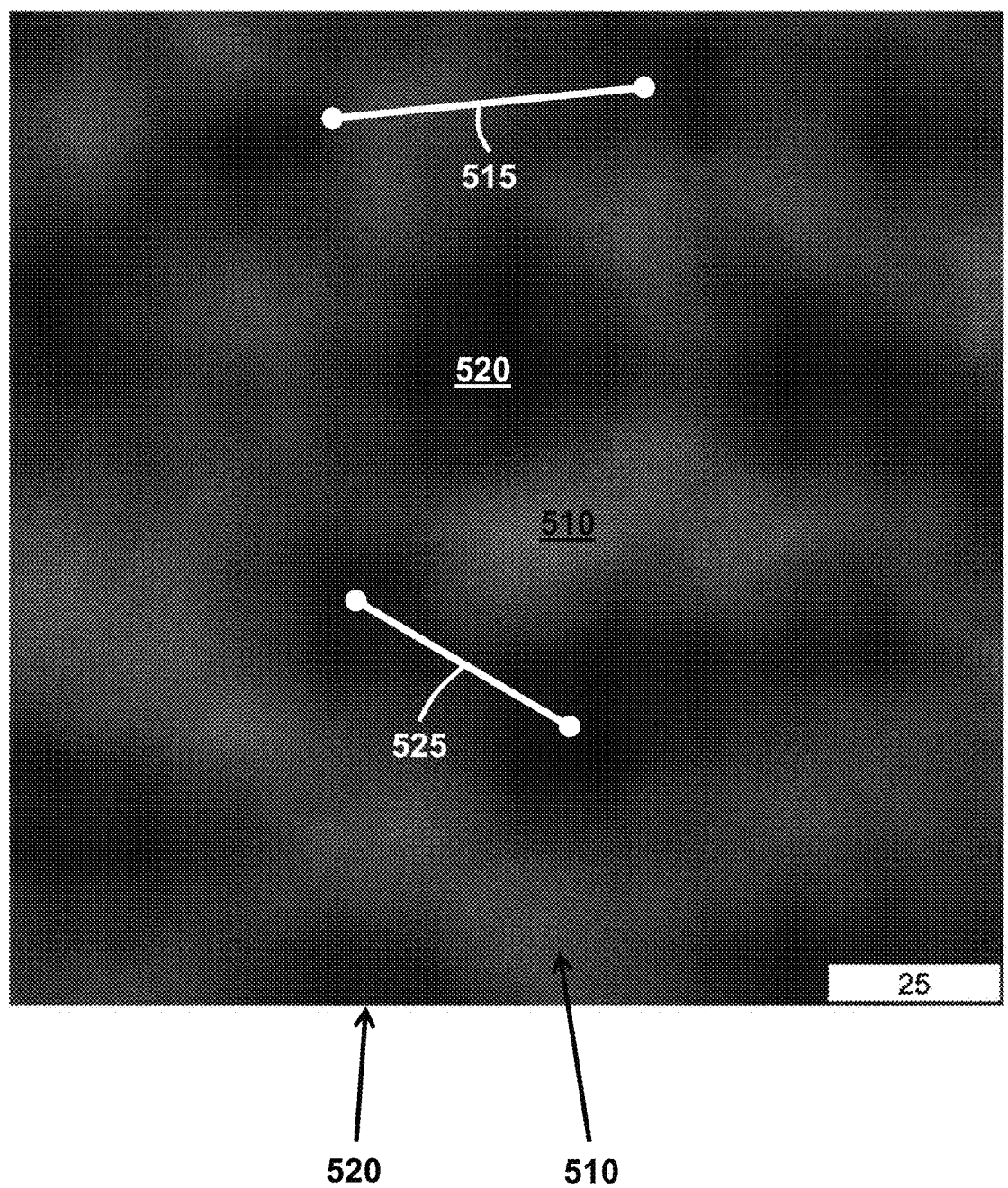
FIG. 5B is a confocal laser scanning microscopy image for the polymer film of Example 3 (scale bar=25 μm).

Confocal microscopy is again employed, using the same procedure as described in Example 1. FIGS. 5A and 5B show confocal laser scanning microscopy (CLSM) images for the polymer film with 25 mol % PEG content. CLSM images are shown at different magnifications of the Example 3 films soaked with water-soluble fluorescent dye.

The fluorescent regions 510 (which display as green regions in the color drawings and lighter regions when reproduced in grayscale) are representative of hydrophilic PEG regions containing a water-soluble fluorescent dye. The inclusions 520 (which display as darker regions) are representative of hydrophobic fluoropolymer regions. The scale bars are 100 μm and 25 μm in FIGS. 5A and 5B, respectively.

Microphase separation is shown in these images. The length scale of phase inhomogeneity for the structure in FIGS. 5A and 5B appears to be in the range of 1 to 100 microns. In particular, the phase inhomogeneity can be characterized by a length scale associated with a discrete phase 520. For example, the length scale of phase inhomogeneity may refer to the average size (e.g., effective diameter) of discrete inclusions of one phase 520 dispersed in a continuous phase 510. The selected (for illustration) inclusions 520 labeled in FIG. 5B have an effective diameter of about 35 microns; generally the inclusions have an effective diameter of about 5 to 100 microns in FIGS. 5A and 5B. The length scale of phase inhomogeneity may refer to the average center-to-center distance 525 between nearest-neighbor inclusions of the same phase 520. In FIG. 5B, the selected center-to-center distance 525 is about 40 microns. The length scale of phase inhomogeneity may alternatively refer to the average separation distance 515 between nearest-neighbor regions of the discrete (e.g., droplets) phase 520, i.e. the size of the continuous phase 510 regions. In FIG. 5B, the selected separation distance 515 is about 50 microns. A range of particle sizes and separations is clearly present in this structure; the specific instances of features 510, 515, 520, and 525 were arbitrarily selected.

As described earlier, emulsified droplets rich in either PEG or PFPE are sprayed or cast from a mixture. Upon addition of a curative and the evaporation of a solvent, these droplets coalesce to form a continuous film that is inhomogeneous on the microscale (1-100 μm). In FIGS. 5A and 5B, the dark PFPE-rich areas form a discrete phase (520) that is hydrophobic in character, while the dyed PEG-rich regions form a continuous phase (510) surrounding the discrete regions.

Example 4: Impedance Spectroscopy of the Example 1, Example 2, and Example 3 Polymer Films The interconnectivity of a single phase through the polymer network is indirectly investigated using electrochemical impedance spectroscopy (EIS). A two-electrode, humidity-controlled electrochemical cell is constructed to measure ionic conductivity through the membrane. Measurements are made on the segmented copolymers of Examples 1, 2, and 3 having 75% PEG content, 50% PEG content, and 25% PEG content, respectively.

Figure 6:
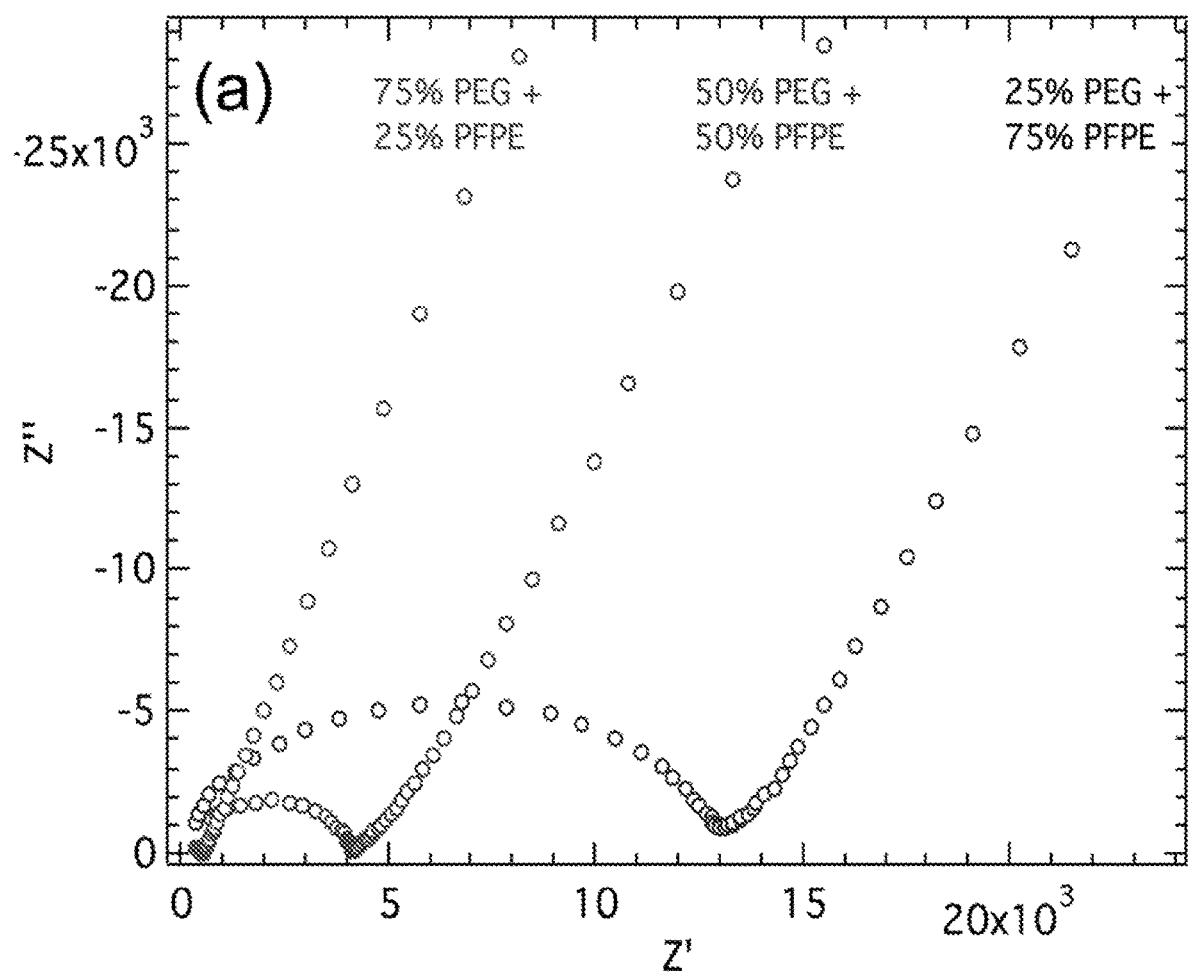
FIG. 6 is a series of Nyquist plots from three humidified polymeric coatings composed of variable concentrations of fluoropolymer and poly(ethylene glycol) flexible segments, in Example 4.
Figure 7:
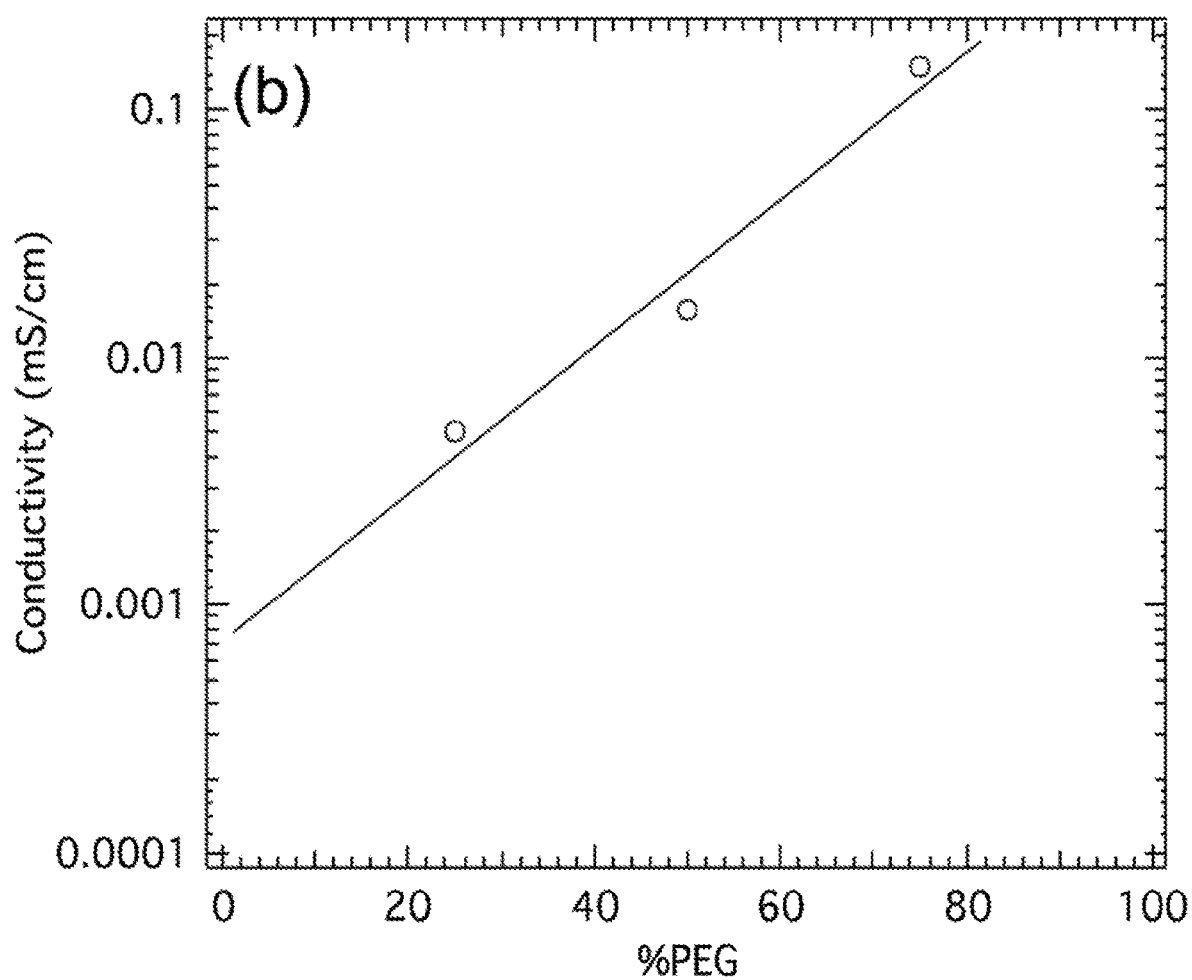
FIG. 7 is a plot of ionic conductivities on a log scale as a function of PEG content, in Example 4. These plots reveal a strong correlation between ionic conductivity and concentration of hygroscopic component (PEG), and indicate continuity of the hygroscopic phase throughout the film.

FIG. 6 shows Nyquist plots from the series of three humidified polymeric coatings composed of variable concentrations of fluoropolymer and poly(ethylene glycol) flexible segments. The real (Z') and imaginary (Z") components of the impedance were measured over a frequency range from $10^6$ Hz to 0.1 Hz. The extrinsic resistance is determined by extrapolating the semicircle and taking the value of Z' at Z"=0. The intrinsic conductivities of the humidified films are determined from the resistance, film thickness, and surface area. The intrinsic conductivities ranged from $5 \times 10^{-6}$ S/cm (25% PEG) to $1.5 \times 10^{-4}$ S/cm (75% PEG) and scaled with PEG content, as shown in FIG. 7. FIG. 7 plots ionic conductivities on a log scale as a function of PEG content. These plots reveal a strong correlation between ionic conductivity and concentration of hygroscopic component (PEG), and indicate continuity of the hygroscopic phase throughout the film.

The same films measured under dry conditions exhibited no measurable conductivity. These results reveal two important points. First, water is incorporated into the hygroscopic PEG phase and is responsible for the high ionic conductivities measured in the humidified samples. Second, the hygroscopic layer (PEG) phase is interconnected and exists throughout the film.

Example 5: Incorporation of Liquid Electrolyte into Example 3 Polymer Film

Here we demonstrate that a liquid electrolyte can be incorporated into a multiphase polymer network to significantly enhance the ionic conductivity, without altering the structure of the network. Three films of identical composition, containing 25% PEG and 75% fluoropolymer (from Example 3), are prepared. One film is soaked in deionized water for 24 hr. A second film is exposed to 100% humidity (no soak or wash). A third film is soaked in an electrolyte solution of 1 M NaCl+$H_2O$ (deionized water, i.e. DI water) solution for 24 hr. The three films are blotted dry and inserted into a 2-electrode electrochemical cell under ambient humidity.

Figure 8:
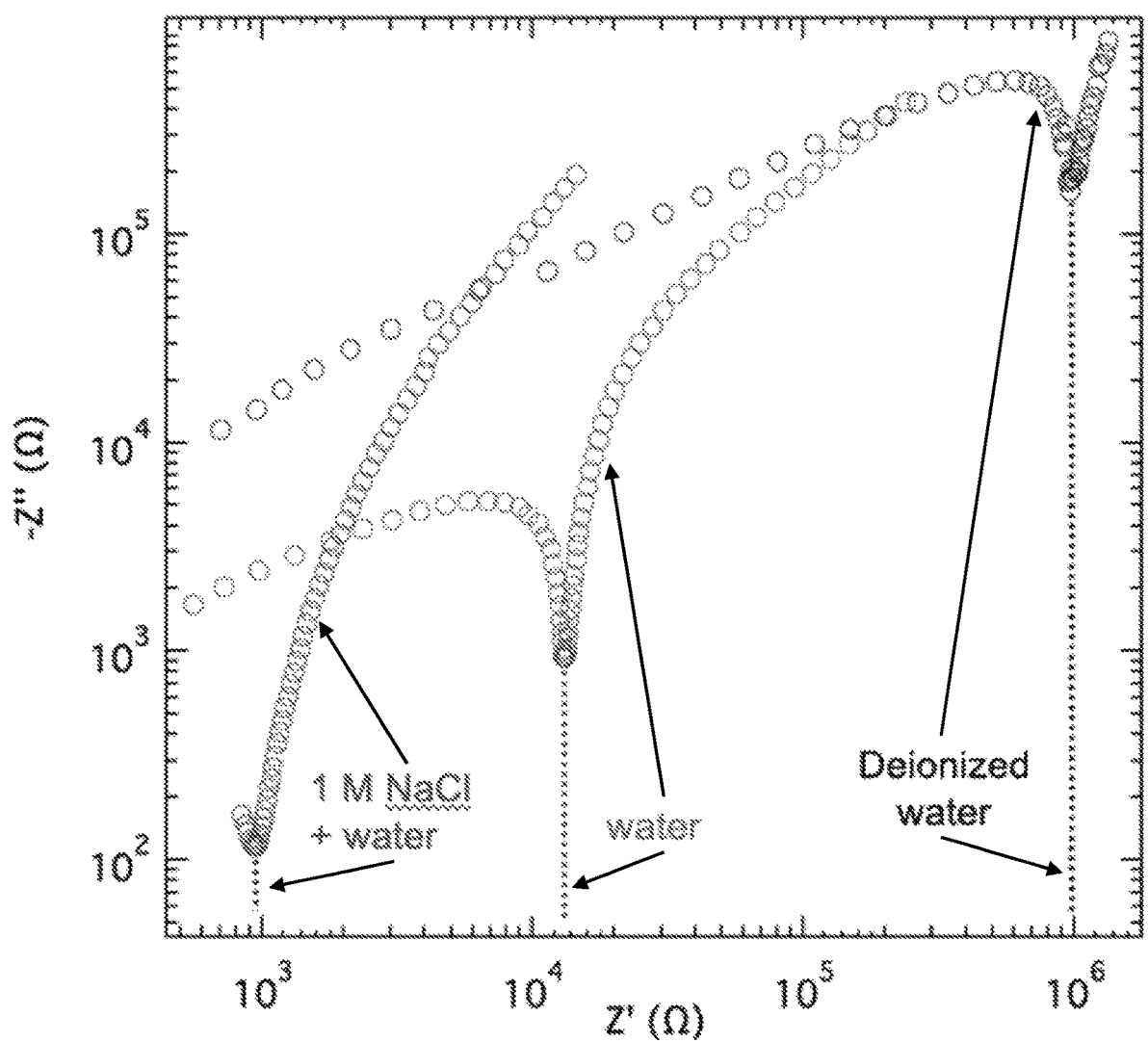
FIG. 8 is a series of Nyquist plots for three polymer films of Example 5, on a log-log scale with a dashed line indicating the film resistance.

FIG. 8 shows Nyquist plots for the three films, on a log-log scale with a dashed line indicating the film resistance. An increase in ionic conductivity of over three orders of magnitude is observed between the film soaked in DI water (~1.6×10$^{-8}$ S/cm) and the film soaked in 1 M NaCl (~2.1×10$^{-5}$ S/cm).

These results demonstrate a composition comprising a first solid material and a second solid material that are chemically distinct, wherein the first solid material and the second solid material are microphase-separated; and a liquid electrolyte selectively absorbed into the first solid material (PEG phase). The composition properties can be modified by tailoring the incorporated liquid(s).

Depending on the nature of the liquid additive, relevant applications exist in automotive and aerospace including enhanced performance with anti-fouling and anti-corrosion properties. Additionally, potential applications lie in the area of energy storage. The basis of the technology addresses the issue of scale and durability, employing chemistry and application methods compatible with commercial production processes. The compositions provided herein have economic scalability for both the synthesis (e.g., self-organizing polymer domains) and application of the coating (e.g., spray coating).

In this detailed description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A composition comprising:
a first solid material and a second solid material that are chemically distinct, wherein said first solid material and said second solid material are microphase-separated on a microphase-separation length scale from about 0.2 microns to about 500 microns, wherein said first solid material and said second solid material have different surface energies, wherein one of said first solid material and said second solid material is a hydrophobic material, and the other of said first solid material and said second solid material is a hydrophilic or hygroscopic material, and wherein said first solid material and said second solid material are both present as phase-separated regions of a segmented copolymer; and at least one liquid selectively absorbed, with a selectivity of at least 60%, into either of said first solid material or said second solid material.

2. The composition of claim 1, wherein said liquid is a freezing-point depressant for water.

3. The composition of claim 2, wherein said liquid is selected from the group consisting of methanol, ethanol, isopropanol, ethylene glycol, propylene glycol, glycerol, poly(ethylene glycol), and combinations, isomers, or homologous species thereof.

4. The composition of claim 1, wherein said liquid is a lubricant.

5. The composition of claim 4, wherein said liquid is selected from the group consisting of fluorinated oils, fluorocarbon ether polymers of polyhexafluoropropylene, siloxanes, petroleum-derived oils, mineral oil, plant-derived oils, canola oil, soybean oil, and combinations thereof.

6. The composition of claim 1, wherein said liquid is or includes water.

7. The composition of claim 1, wherein said liquid contains a solid lubricant suspended or dissolved in said liquid.

8. The composition of claim 1, wherein said liquid is an electrolyte.

9. The composition of claim 8, wherein said liquid is selected from the group consisting of poly(ethylene glycol), ionic liquids, dimethyl carbonate, diethyl carbonate, methyl ethyl dicarbonate, and combinations thereof.

10. The composition of claim 1, wherein said liquid is present in said composition at a concentration from about 5 wt % to about 50 wt %.

11. The composition of claim 1, wherein said composition further comprises an additional liquid selectively absorbed into the other of said first solid material or said second solid material that does not contain said at least one liquid.

12. The composition of claim 1, wherein said microphase-separation length scale is from about 0.5 microns to about 100 microns.

13. The composition of claim 1, wherein said first solid material and said second solid material further are nanophase-separated on a nanophase-separation length scale from about 10 nanometers to about 100 nanometers, and wherein said nanophase-separation length scale is hierarchically distinct from said microphase-separation length scale.

14. The composition of claim 1, wherein one of said first solid material and said second solid material is present as a plurality of discrete inclusions dispersed within a continuous matrix comprising the other of said first solid material and said second solid material.

15. The composition of claim 1, wherein said hydrophobic material has a surface energy from about 5 mJ/m$^2$ to about 50 mJ/m$^2$.

16. The composition of claim 1, wherein said hydrophobic material is a fluoropolymer.

17. The composition of claim 1, wherein said segmented copolymer is a urethane-urea copolymer.

18. The composition of claim 1, wherein said segmented copolymer includes:
(a) one or more first soft segments selected from fluoropolymers having an average molecular weight from about 500 g/mol to about 20,000 g/mol, wherein said fluoropolymers are (α,ω)-hydroxyl-terminated and/or (α,ω)-amine-terminated;
(b) one or more second soft segments selected from polyesters or polyethers, wherein said polyesters or polyethers are (α,ω)-hydroxyl-terminated and/or (α,ω)-amine-terminated;

(c) one or more isocyanate species or a reacted form thereof, possessing an isocyanate functionality of 2 or greater; and
(d) one or more polyol or polyamine chain extenders or a reacted form thereof.

19. The composition of claim 1, wherein said segmented copolymer includes:
(a) fluoropolymers having an average molecular weight from about 500 g/mol to about 20,000 g/mol, wherein said fluoropolymers are (α,ω)-hydroxyl-terminated and/or (α,ω)-amine-terminated, and wherein said fluoropolymers are present in the triblock structure:

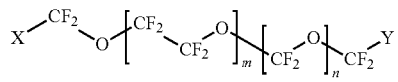

wherein:
X, Y=CH$_2$—(O—CH$_2$—CH$_2$)$_p$-T, and X and Y are independently selected;
p=1 to 50;
T is a hydroxyl or amine terminal group;
m=1 to 100; and
n=1 to 100;
(b) one or more isocyanate species possessing an average isocyanate functionality of about 2 or greater, or a reacted form thereof; and
(c) one or more polyol or polyamine chain extenders or crosslinkers optionally possessing an average functionality of about 3 or greater, or a reacted form thereof.

20. The composition of claim 1, wherein said composition is present in a coating.

21. The composition of claim 20, wherein said coating is an anti-ice coating, an anti-bug coating, and/or an anti-friction coating.

22. The composition of claim 1, wherein said composition is present in an energy-transfer material or an energy-storage material.

23. The composition of claim 1, wherein said selectivity is at least 75%.

24. The composition of claim 1, wherein said selectivity is at least 90%.

* * * * *